United States Patent
Karp et al.

(10) Patent No.: US 11,524,024 B2
(45) Date of Patent: Dec. 13, 2022

(54) COMPOUNDS TO MODULATE INTESTINAL ABSORPTION OF NUTRIENTS

(71) Applicant: The Brigham and Women's Hospital, Inc., Boston, MA (US)

(72) Inventors: Jeffrey M. Karp, Brookline, MA (US); Yuhan Lee, Cambridge, MA (US); Ali Tavakkoli, Boston, MA (US); Tarawatie E. Deelman, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 16/890,913

(22) Filed: Jun. 2, 2020

(65) Prior Publication Data
US 2020/0289546 A1    Sep. 17, 2020

Related U.S. Application Data

(63) Continuation of application No. 14/776,594, filed as application No. PCT/US2014/026007 on Mar. 13, 2014, now Pat. No. 10,716,802.
(Continued)

(51) Int. Cl.
*A61K 31/7135*   (2006.01)
*A61K 9/50*   (2006.01)
(Continued)

(52) U.S. Cl.
CPC ........ *A61K 31/7135* (2013.01); *A61K 9/1611* (2013.01); *A61K 9/1623* (2013.01); *A61K 9/5036* (2013.01); *A61K 33/18* (2013.01); *A61K 33/20* (2013.01); *A61K 33/38* (2013.01); *A61K 9/4808* (2013.01)

(58) Field of Classification Search
None
See application file for complete search history.

(56) References Cited

U.S. PATENT DOCUMENTS

| | | |
|---|---|---|
| 3,432,489 A | 3/1969 | Nitta et al. |
| 4,522,811 A | 6/1985 | Eppstein et al. |

(Continued)

FOREIGN PATENT DOCUMENTS

| | | |
|---|---|---|
| CA | 2067070 | 10/1992 |
| EP | 0511703 | 11/1992 |

(Continued)

OTHER PUBLICATIONS

NIH. National Cancer Institute "gastrointestinal tract" < https://www.cancer.gov/publications/dictionaries/cancer-terms/def/gastrointestinal-tract> accessed Nov. 18, 2021 (Year: 2018).*

(Continued)

*Primary Examiner* — Nicole P Babson
(74) *Attorney, Agent, or Firm* — Fish & Richardson P.C.

(57) ABSTRACT

This disclosure relates to compositions including formulated sucralfate or other aluminum-crosslinked sulfated agents for the modulation of nutrient absorption through the intestinal lining as well as methods for the manufacture of and the use of these compounds for treating disorders requiring a modulation of certain nutrients to the body including diabetes type II and clinical obesity.

25 Claims, 18 Drawing Sheets

Related U.S. Application Data

(60) Provisional application No. 61/794,362, filed on Mar. 15, 2013.

(51) Int. Cl.
    *A61K 33/20*     (2006.01)
    *A61K 33/38*     (2006.01)
    *A61K 33/18*     (2006.01)
    *A61K 9/16*     (2006.01)
    *A61K 9/48*     (2006.01)

(56) References Cited

U.S. PATENT DOCUMENTS

| | | |
|---|---|---|
| 4,866,856 A | 9/1989 | Feeley |
| 4,885,281 A | 12/1989 | Hanstein et al. |
| 5,013,557 A | 5/1991 | Tai |
| 5,246,697 A | 9/1993 | Conte et al. |
| 5,294,434 A | 3/1994 | King et al. |
| 5,321,013 A | 6/1994 | Zagnoli et al. |
| 5,464,828 A | 11/1995 | Katayama et al. |
| 5,563,258 A | 10/1996 | Ochi et al. |
| 5,595,977 A | 1/1997 | Dyrsting et al. |
| 5,661,137 A | 8/1997 | Zagnoli |
| 5,718,923 A | 2/1998 | Matsuda et al. |
| 5,968,906 A | 10/1999 | Kashimura et al. |
| 6,391,294 B1 | 5/2002 | Dettmar et al. |
| 6,391,860 B1 | 5/2002 | McGrath |
| 6,555,137 B1 | 4/2003 | Yamazaki et al. |
| 6,773,722 B2 | 8/2004 | Zagnoli et al. |
| 10,716,802 B2 | 7/2020 | Karp et al. |
| 10,973,846 B2 | 4/2021 | Karp et al. |
| 2007/0190139 A1 | 8/2007 | Zerbe et al. |
| 2008/0319230 A1 | 12/2008 | Sigl et al. |
| 2009/0196896 A1 | 8/2009 | Patton et al. |
| 2010/0172967 A1 | 7/2010 | Nemoto et al. |
| 2011/0021455 A1 | 1/2011 | Chesnoy et al. |
| 2011/0229556 A1 | 9/2011 | Irvine et al. |
| 2012/0039981 A1 | 2/2012 | Pedersen et al. |
| 2012/0064139 A1 | 3/2012 | McGrath et al. |
| 2013/0274209 A1 | 10/2013 | Colombo |
| 2016/0022729 A1 | 1/2016 | Karp et al. |
| 2020/0046754 A1 | 2/2020 | Karp et al. |

FOREIGN PATENT DOCUMENTS

| | | |
|---|---|---|
| EP | 0245855 | 1/1993 |
| EP | 0437406 | 3/1993 |
| EP | 2482822 | 8/2012 |
| RU | 2422133 | 6/2011 |
| WO | WO 1989/005645 | 6/1989 |
| WO | WO 2011/041509 | 4/2011 |
| WO | WO 2014/151565 | 9/2014 |

OTHER PUBLICATIONS

Beheshti et al., "Comparison of topical sucralfate and silver sulfadiazine cream in second degree burns in rats," Adv Clin Exp Med, 2013, 22: 481-487.

Couzin, "Bypassing Medicine to Treat Diabetes," Science, 2008, 320: 438-440.

Cummings and Flum, "Gastrointestinal Surgery as a Treatment for Diabetes," J. Am. Med. Assoc., 2008, 299: 341-343.

en.wikipedia.org [online]. "Freeze-drying," dated Sep. 18, 2015 [retrieved on Nov. 22, 2016], Retrieved from the Internet <URL: https://en.wikipedia.org/w/index.php?title=Freezedrying&oldid=681682674> 7 pages.

en.wikipedia.org [online]. "Coacervate," dated May 20, 2015 [retrieved on Nov. 22, 2016]. Retrieved from the Internet <URL: https://en.wikipedia.org/w/index.php?title=Coacervate&oldid=663181907> 2 pages.

en.wikipedia.org [online]. "List of water-miscible solvents," dated Mar. 31, 2015[retrieved on Nov. 22, 2016]. Retrieved from the Internet <URL: https://en.wikipeda.org/w/index.php?title=list_ofwater-miscible_solvents&oldid=654319850> 3 pages.

en.wikipedia.org [online]. "Propylene glycol," dated Sep. 19, 2015 [retrieved on Nov. 22, 2016]. Retrieved from the Internet <URL: https://en.wiklpedia.org/w/index.php?title=Propylene_glycol&oldid=681710532> 7 pages.

EP Extended European Search Report in Application No. 16849871.5, dated May 7, 2019, 10 pages.

EP Office Action in European Appln. No. 16849871, dated Jun. 24, 2020, 8 pages.

Gersin et al., "Open-label, sham-controlled trial of an endoscopic duodenojejunal bypass liner for preoperative weight loss in bariatric surgery candidates," Gastrointest. Endosc. 2010, 71: 976-82.

Gupta et al., "Topical Sucralfate Treatment of Anal Fistulotomy Wounds: A Randomized Placebo-Controlled Trial," Diseases of the Colon & Rectum, 2011, 54: 699-704.

Higo et al., "A Novel Evaluation Method of Gastric Mucoadhesive Property in Vitro and the Mucoadhesive Mechanism of Tetracycline-Sucralfate Acidic Complex for Eradication of Helicobacter pylori," Pharm. Res, 2004, 21: 413-419.

Malbert et al., "Duodenal Bulb Control of the Flow Rate of Digesta in the Fasted and Fed Dog," J. Physiol., 1989, 409:371-384.

Markham et al., "Topical sucralfate for erosive irritant diaper dermatitis," Archives of Dermatology, 2000, 136: 1199-200.

New et al., "Assessing the prevalence, monitoring and management of chronic kidney disease in patients with diabetes compared with those without diabetes in general practice," Diabetic Medicine, 2007, 24: 364-369.

Ochi, "Chemistry of Sucralfate" in Sucralfate: From Basic Science to the Bedside, Chapter 5, 1995, pp. 53 and 55.

PCT International Preliminary Report on Patentability in International Application No. PCT/US2016/053781, dated Apr. 5, 2018, 8 pages.

PCT International Preliminary Report on Patentability in International Application No. PCT/US2014/26007, dated Sep. 15, 2015, 9 pages.

PCT International Search Report and Written Opinion in International Application No. PCT/US2016/053781, dated Jan. 26, 2017, 15 pages.

PCT International Search Report and Written Opinion in International Application No. PCT/US2014/26007, dated Jul. 7, 2014, 16 pages.

Pories et al., "Who Would Have Thought It? An Operation Proves to Be the Most Effective Therapy for Adult-Onset Diabetes Mellitus," Ann. Surg., 1995, 222: 339-350.

Ritz et al., "Nephropathy in patients with type 2 diabetes mellitus," New Engl. J. Med., 1999, 341: 1127-1133.

RU English translation of RU 2422133 01 (Year: 2011).

Rubino et al., "Potential of Surgery for Curing Type 2 Diabetes Mellitus," Ann. Surg., 2002, 236: 554-559.

Schouten et al., "A multi-center, randomized efficacy study of th EndoBarrier™ Gastrointestinal Liner for pre-surgical weight loss prior to bariatric surgery," Ann. Surg., 2010, 251(2), 236-243.

Slomiany et al., "Enhancement of the protective qualities of gastric mucus by sucralfate: Role of phosphoinositides," Am. J. of Med., 1991, 91: 30S-36S.

Tasman-Jones et al., "Sucralfate interactions with gastric mucus," Am. J. Med., 1989, 86: 5-9.

U.S. Office Action in U.S. Appl. No. 14/776,594, dated Jan. 18, 2017, 12 pages.

U.S. Office Action in U.S. Appl. No. 14/776,594, dated Nov. 28, 2017, 12 pages.

U.S. Office Action in U.S. Appl. No. 14/776,594, dated May 8, 2019, 13 pages.

U.S. Office Action in U.S. Appl. No. 15/763,018, dated Aug. 19, 2020, 29 pages.

www.chemicaprocessing.com [online]. "Marion Mixers: Comparing Microwave to Conventional Heating and Drying Systems," dated Jun. 12, 2015 [retrieved on Nov. 22, 2016]. Retrieved from the Internet <URL: http://www.chemicalprocessing.com/assets/wp_downloads/pdf/comparing-microwave-tocovnetional-heating-drying-systems-v2.pdf > 7 pages.

(56) References Cited

OTHER PUBLICATIONS www.puecchner.com [online]. "Microwave Vacuum Drying for advanced Process Technology," Oct. 29, 2012 [retrieved on Nov. 22, 2016). Retrieved from the Internet <URL: http://www.pueschner.com/downloads/vacuumdrying.pdf> 8 pages.
Zuidam and Shimoni, "Overview of Microencapsulates for Use in Food Products or Processes and Methods to Make Them in Encapsulation Technologies for Active Food Ingredients and Food Processing," Chapter 2, 2010, p. 15.

\* cited by examiner

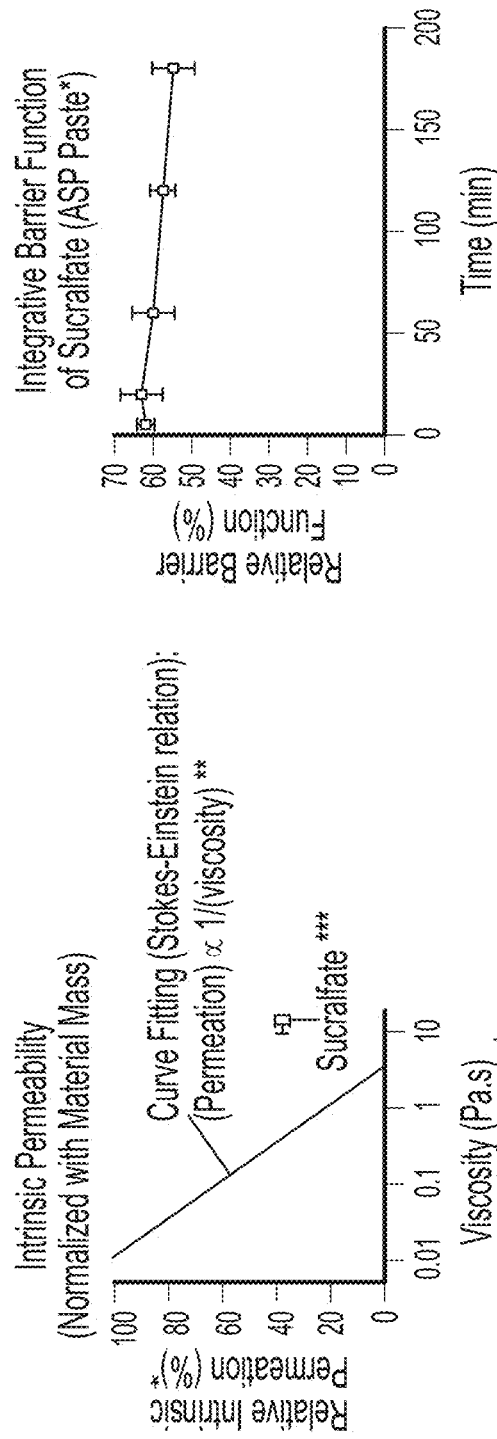
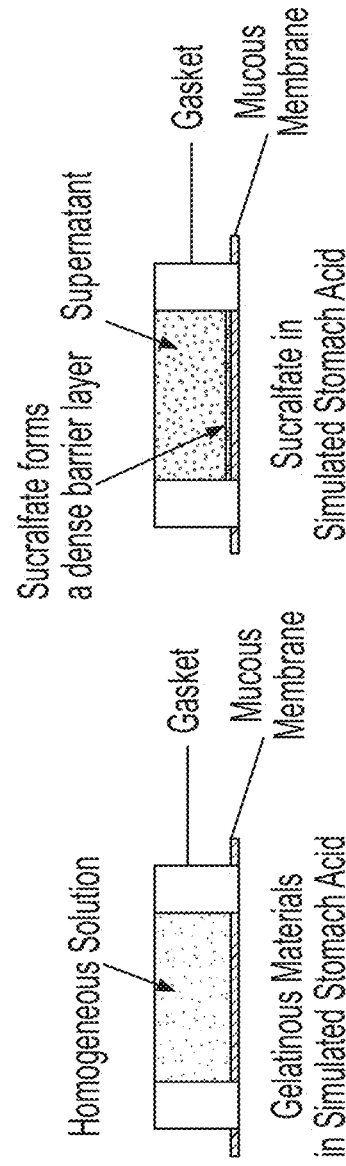
FIG. 4A
FIG. 4B
FIG. 4C

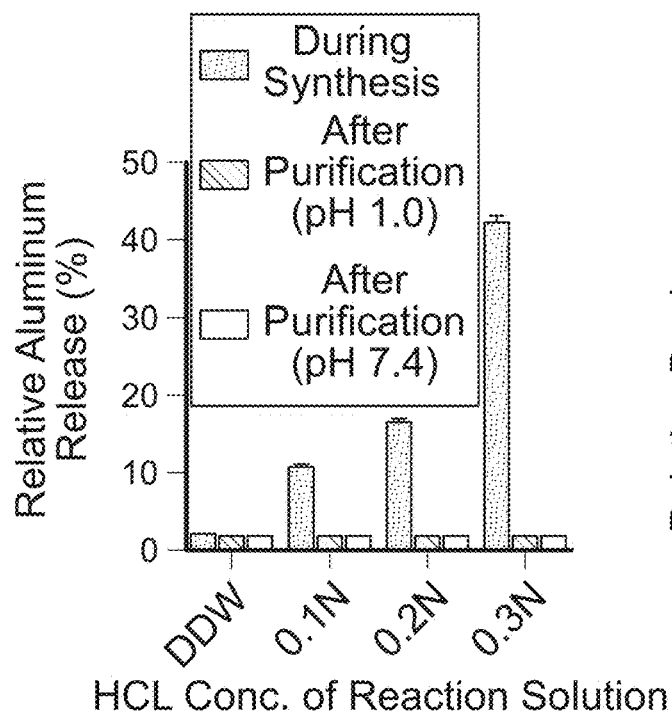
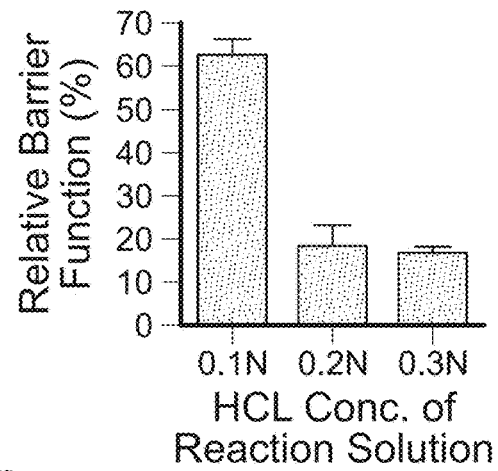
FIG. 6B
FIG. 6C
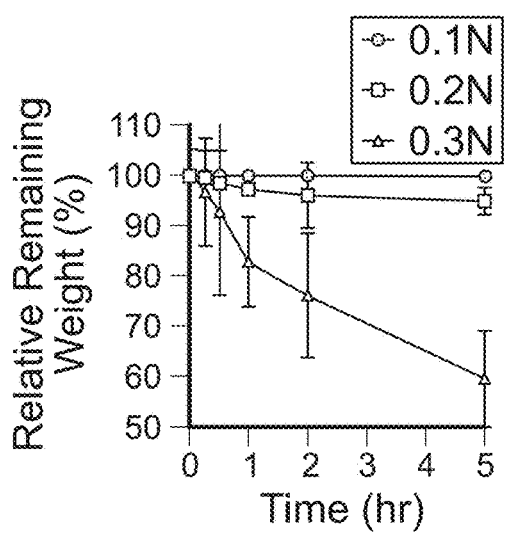
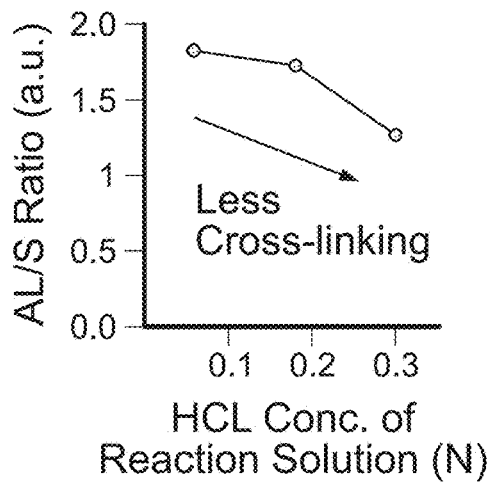
FIG. 6D
FIG. 6E
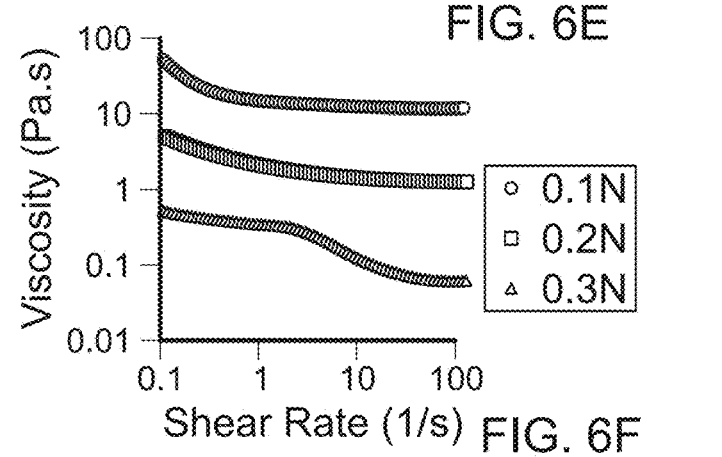
FIG. 6F

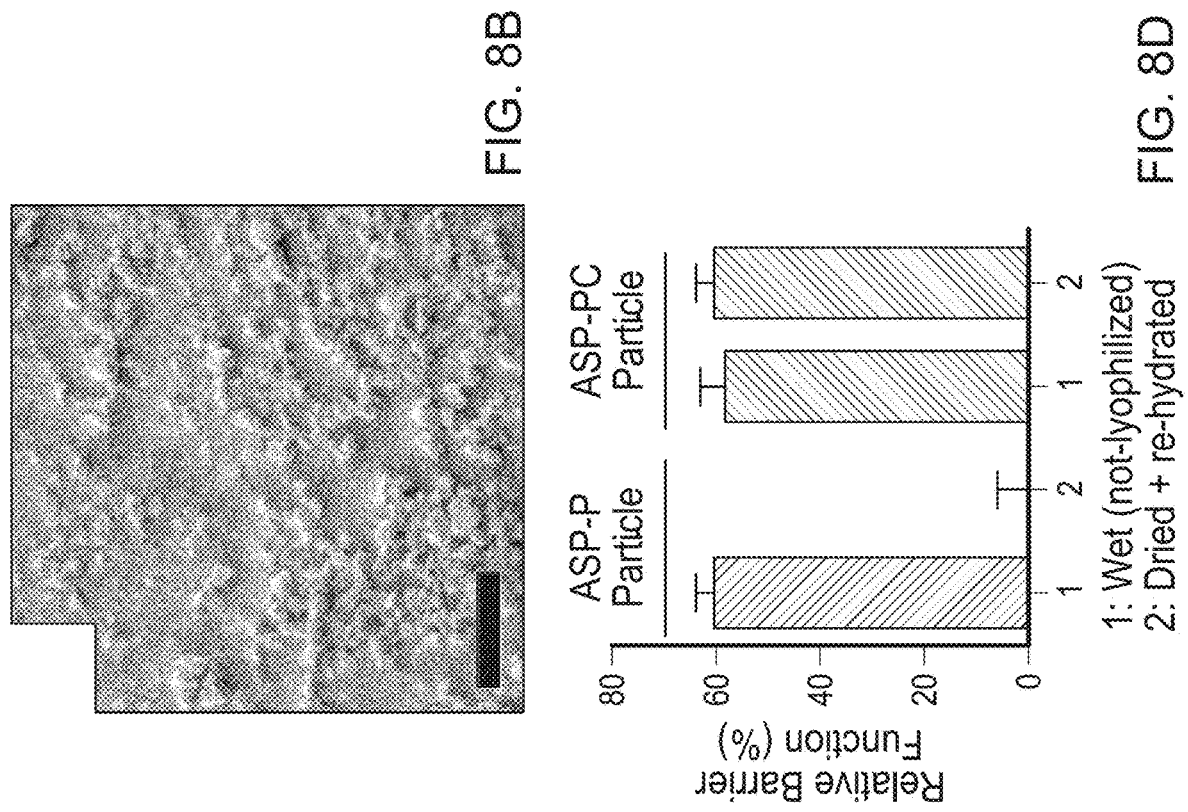
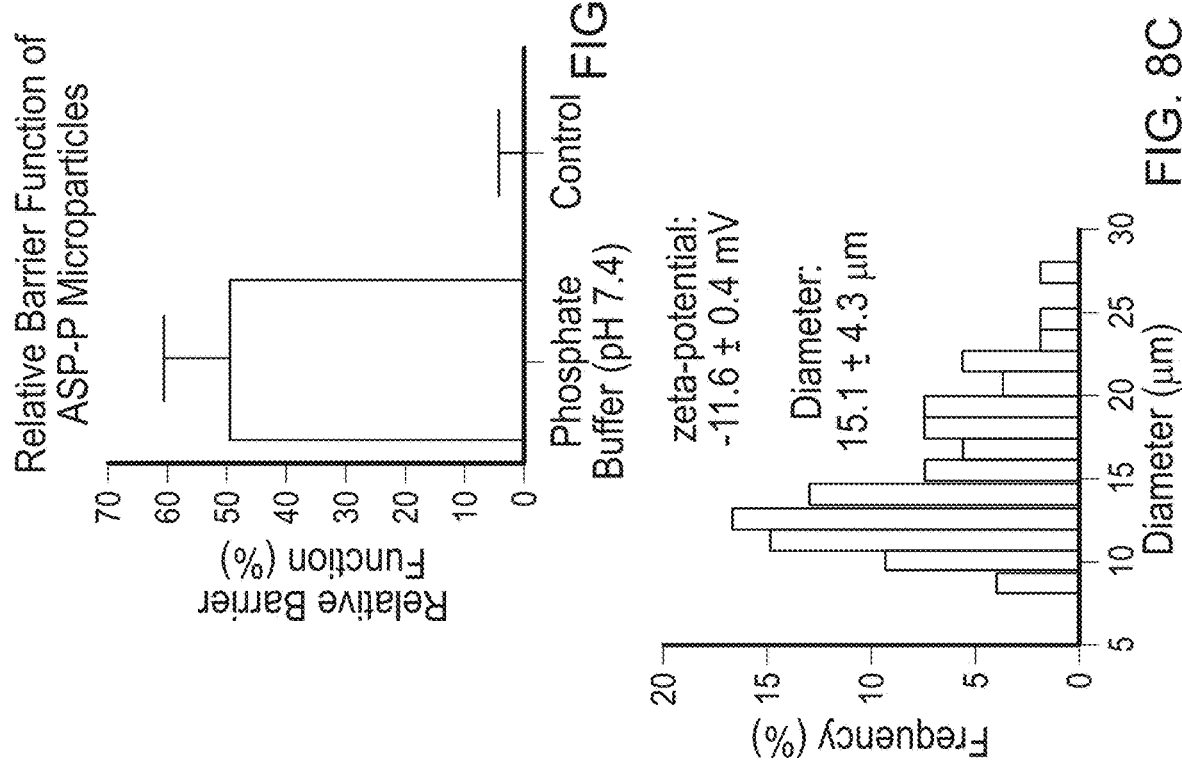

COMPOUNDS TO MODULATE INTESTINAL ABSORPTION OF NUTRIENTS

CROSS-REFERENCE TO RELATED APPLICATIONS

This application is a continuation of U.S. patent application Ser. No. 14/776,594, filed Sep. 14, 2015, which is a U.S. National Phase Application under 35 U.S.C. § 371 of International Patent Application No. PCT/US2014/026007, filed on Mar. 13, 2014, which claims priority to U.S. Provisional Patent Application Ser. No. 61/794,362, filed Mar. 15, 2013, the contents of each of which are incorporated herein by reference in their entireties.

FIELD OF THE INVENTION

The field of this disclosure relates to microparticulate compositions that modulate absorption of nutrients through the intestinal lining by forming a barrier on the intestine wall.

BACKGROUND

Type-2 diabetes mellitus (T2DM) affects about 11.3% of the U.S. adult population with 35% of the U.S. adults having pre-diabetic symptoms. U.S. healthcare costs due to diabetes exceed $174 billion annually. The incidence of T2DM continues to increase in parallel with the obesity epidemic, and the present treatment algorithm for T2DM consists of a regimen of medication that is suboptimal for many patients. Current strategies for T2DM management and treatment range from commercial diets and drugs to surgical approaches. Although each of these strategies may have merit, considerable limitations exist. While diets carry limited risk, they are often unsuccessful. Drugs that lower blood glucose level (e.g., metformin) are also available, but the use and success of these drugs are limited due to side effects, poor compliance, and low efficacy. Patients also have options of bariatric surgeries including laparoscopic adjustable gastric banding (LAGB), bilio-pancreatic diversion (BPD), laparoscopic sleeve gastrectomy (LSG), and Roux-en-Y bypass (RYGB) (W. J. Pories et al., Ann. Surg.,222, 339-350 (1995); F. Rubino et al., Ann. Surg., 236, 554-559, (2002); J. Couzin, Science, 320, 438-440 (2008); D. E. Cummings and D. R. Flum, J. Am. Med. Assoc. 299, 341-343 (2008)).

Originally developed for weight loss, RYGB surgery has been recognized as the gold standard bariatric operation to treat obesity-related T2DM. Multiple reports have confirmed that obese T2DM patients who undergo RYGB surgery immediately experience significant improvement or complete resolution of their T2DM prior to any significant weight loss. Accordingly, many have classified RYGB as a "metabolic" operation and a "cure" for T2DM. However, over 70% of patients, although overweight or mildly obese, do not meet the NIH criteria for weight loss surgery and struggle with sub-optimal medical treatments (American Diabetes Association. V. Diabetes Care. Diabetes Care, 35 (2012)).

This result highlights the need for less invasive alternatives that replicate the metabolic success of RYGB and that can be offered to a wider patient population. The success of RYGB in remitting T2DM has inspired significant research into mechanisms underlying this observation with significant interest in the role of duodenal isolation. As a less invasive implantable alternative to RYGB, a duodeno-jejunal bypass sleeve (DJBS) was developed to prevent contact between food and duodenal mucosa, and has shown promising results in remitting T2DM. However, the sleeve implant requires placements using endoscopy, and is associated with a high rate of bleeding or obstruction, and requires annual device removal (R. Schouten et al., Ann. Surg.,251(2), 236-243 (2010); K. S. Gersin et al., Gastrointest. Endosc. (2010)). Therefore, there is a clear and urgent need for a less invasive T2DM treatment option that is easy to administer and does not present risks associated with surgical procedures.

SUMMARY

The present disclosure describes compositions that can be utilized to temporarily coat the lining of portions of the gastrointestinal tract (e.g., proximal gastrointestinal tract) to thereby modulate absorption of nutrients, such as glucose, through the intestinal lining into the bloodstream. Various medical conditions (e.g., obesity, type II diabetes (T2DM), and pre-diabetes) can be treated or can benefit from a reduction in the absorption of nutrients (e.g., glucose) that can be achieved by generating a barrier that decreases absorption of the nutrients by the tissue. Thus, the present disclosure also describes therapeutic methods using such compositions to treat disorders such as obesity and diabetes.

In general, in one aspect the disclosure includes compositions that include, consist essentially of, or consist of particles including aluminum cross-linked sulfated agents, such as sucralfate, and a particle stabilizer, optionally combined with, e.g., cross-linked together with a humectant (e.g., a crosslinking humectant). In some embodiments, the particles include aluminum cross-linked sulfated agent (e.g., sucralfate) is cross-linked with a crosslinking humectant with the particle stabilizer present (e.g., substantially present) on the outside surface of the particles (e.g., such that the particle stabilizer prevents aggregation and/or is not cross-linked). In some embodiments, the sulfated agent is sucralfate. Some embodiments of the compositions provided herein further include, consist of, or consist essentially of, a liquid carrier and/or a pH-sensitive material (e.g., a cationic or anionic methacrylate copolymer). In some embodiments, the humectant or crosslinking humectant can include, consist of, or consist essentially of, e.g., carrageenan, propylene glycol, 1,2,6-hexanetriol, butylene glycol, dipropylene glycol, hexylene glycol, glycerin, triethylene glycol, erythritol capryl glycol, phytantriol, hexanediol beeswax, hexanetriol beeswax, panthenol, sodium pyrollidone carboxylic acid, hyaluronic acid, inositol, glycogen, sorbitol, polyglyceryl sorbitol, glucose, fructose, xylitol, elastin, collagen, silk, keratin, isoceteth, isolaureth, laneth, laureth, steareth, polyethylene glycol, silicon copolymers, ammonium lactate, glyceryl triacetate, hydrolyzed collagen, hydrolyzed elastin, hydrolyzed keratin, hydrolyzed silk, lactic acid, manitol, panthenol, polydextrose, propylene glycerol, quilaia, urea, or betaine.

In some embodiments, the humectant or cross-linking humectant is a sulfated agent (e.g., sulfated dextran, sulfated dextrin, sulfated amylopectin, sulfated amylose, sulfated cellulose, carrageenan, chondroitin sulfate, glucose sulfate, sucrose sulfate, and raffinose sulfate. In some embodiments, the particle stabilizer is selected from the group of phosphate ions, pectin, carrageenan, chitosan, cellulose derivatives, gellan gum, alginate, gum karaya, dextran, pullulan, polyethylene glycol (PEG), polyvinyl alcohol (PVA) beeswax, sodium borate, stearic acid, carbomer, cetyl alcohol, propylene glycol, polysorbate, lecithin, glyceryl monostearate, acetic esters of fatty acid, lactic esters of fatty acid, citric esters of fatty acid, tartaric esters of fatty acid, acetyltartaric esters of fatty acid, sucroglycerides, polyglycerol esters of fatty acid, propane-2,3-diol esters of fatty acid, sodium stearoyl-2-lactylate, calcium stearoyl-2-lactylate, stearyl tartate, and castor oil derivatives.

In some embodiments, the composition is provided in a dry form. In some embodiments, the composition can be re-hydrated by addition of water while retaining particle size within 20% (e.g., within 15%, within 10%, or within 5%). In some embodiments, the particles range in size from about 0.1 to 500 (e.g., between 1.0 and 300, between 5.0 and 250, or between 10 and 200) microns.

In some embodiments, the composition is a dry mucoadhesive composition that following hydration stably adheres to a mucin-coated surface under sheer stress conditions. In some embodiments, when hydrated, the composition forms a barrier that when prepared at 10 mg/mL and applied to 1 $cm^2$ surface area cellular nitrate filter (e.g., mucin-coated cellulose nitrate filter) with 0.45 micron holes in a Franz diffusion chamber exhibits less than 60% (e.g., between 5% and 60%, between 10% and 55%, between 15% and 50%, or between 20% and 45%) permeation. In some embodiments, the composition releases less than <0.5% (e.g., between 0.1% and 0.45%, between 0.15% and 0.4%, or between 0.2% and 0.35%) aluminum by weight. In some embodiments, the nutrient barrier properties to glucose to glucose do not appreciably change when the composition is dried and re-hydrated in stomach acid (e.g., first dried and then re-hydrated in stomach acid).

Also provided are methods of making a stabilized sucralfate composition that include, consist of, or consist essentially of mixing sucralfate with humectant or cross-linking humectant, adding acid to the sucralfate and humectant or crosslinking humectant to form a treated sucralfate with a reduced aluminum content, removing excess acid, adding a particle stabilizer, and forming a composition into stabilized sucralfate particles. In some embodiments, the steps of adding a particle stabilizer and forming a composition into stabilized sucralfate particles can happen at substantially the same time (e.g., simultaneously). In some embodiments, the particles are formed by vortexing, homogenization, sonication, and/or spray drying. Some embodiments further include, consist of, or consist essentially of drying the particles. In some embodiments, the particles retain their size within a 20% range (e.g., within 15%, within 10%, or within 5%) in average diameter for at least one week after being rehydrated. In some embodiments, upon rehydration, viscosity changes by less than 5-fold (e.g., less than 4-fold, less than 3-fold, less than 2.5-fold, less than 2-fold, or less than 1.5-fold) compared to acid-treated sucralfate without re-dehydration (e.g., without drying). In some embodiments, the compositions provided herein form a paste upon hydration (e.g., re-hyrdation), such as hydration or rehydration in the presence of acid, that has a viscosity that is, e.g., greater than 35 pa·s (e.g., greater than 40, 45, 50, 55, or 60 pa·s). Some embodiments further include placing the stabilized sucralfate particles into a coating material (e.g., gelatin or HPMC, or any combination of the coating materials described herein or known in the art) to form a coating around the particles. Some embodiments further include adding the stabilized sucralfate particles to a food substance or food additive.

Also provided are methods of modulating (e.g., decreasing) nutritional absorption in a subject in need of such treatment (e.g., a subject having a disorder in need of such treatment, e.g., such as type II diabetes (T2DM), obesity, or pre-diabetes). These methods include, consist of, or consist essentially of selecting a subject in need of such treatment (e.g., a subject suffering from a disorder requiring modulation (e.g., decrease) of nutritional adsorption (e.g., obesity, pre-diabetes, or type II diabetes (T2DM)) or a subject in need of weight loss) and administering to the subject a therapeutically effective amount of any of the compositions provided herein. Also provided are compositions including particles including aluminum cross-linked sulfated agents and a particle stabilizer cross-linked together with a humectant for use in modulating (e.g., decreasing) nutritional absorption in a subject in need of such treatment (e.g., a subject having a disorder in need of such treatment, e.g., such as type II diabetes (T2DM), obesity, or pre-diabetes). Also provided are methods of decreasing the risk of developing type II diabetes (T2DM) in a subject having pre-diabetes (e.g., as compared to another subject having pre-diabetes that does not receive treatment or receives a different treatment) that include, consist of, or consist essentially of selecting a subject having pre-diabetes and administered to the selected subject a therapeutically effective amount of any of the compositions provided herein. Also provided are compositions including particles including aluminum cross-linked sulfated agents and a particle stabilizer cross-linked together with a humectant for use in decreasing the risk of developing type II diabetes (T2DM) in a subject having pre-diabetes.

Also provided are methods of promoting weight loss in a subject that include, consist of, or consist essentially of selecting a subject and administering to the selected subject a therapeutically effective amount of any of the compositions provided herein. In some embodiments, the subject is obese, has type II diabetes (T2DM), or is pre-diabetic. In some embodiments, the subject has a BMI of greater than 30, a BMI between about 25 and about 30, a BMI of between about 20 and 25, or a BMI of between about 18.5 and 25. Also provided are compositions including particles including aluminum cross-linked sulfated agents and a particle stabilizer cross-linked together with a humectant for use in promoting weight loss in a subject (e.g., an obese subject, a subject having type II diabetes (T2DM), or a pre-diabetic subject).

Also provided are methods of treating a gastric, stomach, or intestinal ulcer or wound in a subject (e.g., a subject having mucositis, cancer sore(s), ulcerative colitis, or Crohn's disease) that include, consist of, or consist essentially of selecting a subject having an ulcer or wound and administering to the selected subject a therapeutically effective amount of any of the compositions provided herein. Also provided are compositions including particles including aluminum cross-linked sulfated agents and a particle stabilizer cross-linked together with a humectant for use in treating a gastric, stomach, or intestinal ulcer or wound in a subject (e.g., a subject having mucositis, cancer sore(s), ulcerative colitis, or Crohn's disease).

Also provided are methods of treating a microbial infection or colonization in a subject in need of such treatment (e.g., a subject having a disorder in need of such treatment) that include, consist of, or consist essentially of selecting a subject in need of such treatment (e.g., a subject having a disorder requiring treatment of a microbial colonization or infection) and administering to the subject a therapeutically effective amount of any of the compositions described herein. Also provided are compositions including particles including aluminum cross-linked sulfated agents and a particle stabilizer cross-linked together with a humectant for use in treating a microbial infection or colonization in a subject.

In some embodiments of any of these methods, the composition is encapsulated or delivered in a degradable capsule. In some embodiments, the capsule is configured or designed to degrade in a specific portion of the GI tract. In some embodiments, the capsule includes, consists of, or consists essentially of a pH-sensitive material (e.g., a pH-sensitive material that degrades in alkaline conditions). In some embodiments, the composition is altered or selected to allow specific cranio-caudal distribution of the composition. For example, the alteration of the composition is a change in the pH sensitiveness of the composition, a change in the electrostatic charge of the composition, and/or a change in the size of the composition. In some embodiments, the particle is further cross-linked to, attached to (e.g., physically attached), or combined with an antimicrobial agent (e.g., any of the exemplary antimicrobial agents described herein or known in the art). For example, the antimicrobial agent can be selected from the group of iodine, silver ions, and chlorine, or selected from the group of iodine, silver ions, bismuth (e.g., bismuth salicylate), and chlorine.

Also provided are compositions including particles including aluminum cross-linked sulfated agents and a particle stabilizer cross-linked together with a humectant or crosslinking humectant for use in modulating (e.g., decreasing) nutritional absorption in a subject in need of such treatment (e.g., a subject having a disorder in need of such treatment, e.g., such as type II diabetes (T2DM), obesity, or pre-diabetes), decreasing the risk of developing type II diabetes (T2DM) in a subject having pre-diabetes, promoting weight loss in a subject, or treating a microbial infection or colonization in a subject in need thereof.

In some embodiments, the compositions described herein are used in combination with or as a supplement to an additional agent, e.g., a therapeutic agent, to treat disorders such as diabetes, obesity, pre-diabetes, and mucositis. For example, the additional agent can be a therapeutic agent that is known to be useful to treat the disorder. The additional agent also can be an agent that imparts a beneficial attribute to the therapeutic composition (e.g., an agent that affects the viscosity of the composition).

The combination therapies contemplated herein include, for example, administration of one or more compositions as described herein and one or more additional agent(s) in a single pharmaceutical formulation, as well as administration of one or more compositions as described herein and one or more additional agent(s) in separate pharmaceutical formulations. For example, the additional agents can be administered simultaneously or sequentially over a period of time.

For example, in various embodiments, the compositions described herein are administered with one or more of the following diabetes therapeutic agents: insulin, a metformin, sulfonylurea, alpha-glucosidase inhibitor, thiazolidinediones, amylin analog, bile acid sequestrant, DPP-4 inhibitors, dopamine agonist, incretin mimetics, non-sulfonylurea secretagogues, and meglinitides (Repaglinide/Prandin, Nateglinide/Starlix). In other embodiments, the compositions are administered with one or more of the following obesity therapeutic agents: orlistat, lorcaserin, sibutramine, rimonabant, metformin, exenatide, pramlintide (Symlin), and topiramate/phentermine (Qsymia).

The agents set forth herein are for illustrative purposes and not intended to be limiting. The combinations can also include more than one additional agent, e.g., two or three additional agents if the combination is such that the resulting composition can perform its intended function.

The new methods also include the use of the compositions described herein together with one or more surgical procedures, e.g., to reduce weight. For example, in one embodiment, the compositions are administered prior to or following a weight loss surgery including: RYGB, LAGB, BPD, and gastrectomy (e.g., sleeve gastrectomy),In some instances, the compositions are administered in addition to lifestyle changes. The nutrient absorption-reducing compositions are administered with a limited calorie intake diet and exercise. To practice the methods described herein, the compositions having one or more components described herein can be administered orally.

The term "subject" is used throughout the specification to describe an "animal" or a "human." The term "animal" includes, but is not limited to, birds, reptiles, amphibians, and mammals, e.g., humans, other primates, pigs, rodents such as mice and rats, rabbits, guinea pigs, hamsters, cows, horses, cats, dogs, sheep and goats. Preferred subjects are humans, farm animals, and domestic pets such as cats and dogs.

As used herein, the phrase "therapeutically effective amount" refers to the amounts of the compositions described herein that elicit the desired biological or medicinal response including:

(1) inhibiting a disease, condition, or disorder, or one or more symptoms of the disease, disorder, or condition, in an individual who is experiencing or displaying the pathology or symptomatology of the disease, condition or disorder such as in the case of type 2 diabetes mellitus, inhibiting increased plasma glucose levels;

(2) promoting weight loss;

(3) preventing or reducing the risk of developing type II diabetes in a subject having pre-diabetes; or (4) ameliorating the disease or symptoms of the disease; for example, ameliorating a disease, condition, or disorder, or symptom thereof, in an individual who is experiencing or displaying the pathology or symptomatology of the disease, condition, or disorder (i.e., reversing the pathology or symptomatology) such as ameliorating plasma glucose levels.

For example, the following symptoms of diabetes can all be improved by treating a subject with the compositions described herein: ameliorating plasma glucose levels, HbA1c levels, plasma insulin levels, or active or total Glucagon-like peptide (GLP) levels, or eliminating increased thirst, frequent urination, increased hunger, hypertension, hyperlipidemia, weight loss or gain, obesity-related joint problems, high blood pressure, total cholesterol, elevated LDL and triglycerides, metabolic syndrome, fatigue, blurred vision, slow healing sores, frequent infections, or darkened skin AND/OR elicit one or more of the following: increased levels of postprandial active GLP-1 in plasma, decreased levels of postprandial glucose in plasma, increased levels of C-peptide in plasma, decreased levels of appetite sensation measured by Visual Analogue Scale (VAS), decreased levels of 24-hour plasma glucose assessed by Continuous Glucose Monitoring System (CGMS) or weight loss.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The term "kit" refers to pharmaceutical kits useful, for example, in the treatment or prevention of diabetes or obesity, which include one or more containers containing a compound or pharmaceutical composition comprising a therapeutically effective amount of one or more of the compounds described herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The term "polymer" is employed herein to refer to chemical compounds or a mixture of compounds comprised of repeating structural units.

The phrase "mucoadhesion" is employed herein to refer to a form of adhesion between two materials, at least one of which is a mucosal surface. Mucoadhesion typically occurs within the body of a subject.

The term "humectant" refers to a substance that absorbs or helps another substance retain moisture, such as a hygroscopic substance. It has the property to promote water retention in a substance. When incorporated into a compound structure, hydrophilic humectant molecules increase efficacy of hydration. A crosslinking humectant isan effective cross-linker or spacer that connects different components of a compound.

The phrase "oral glucose tolerance test" refers to a diagnostic assay in which blood samples are obtained from a subject or patient following glucose administration to determine time to clearance of the glucose from the subject's or patient's system. The test is commonly utilized in determining the presence of diabetes or insulin resistance in a subject or patient. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1A is a drawing showing the dispersal of the dry particles in the presence of acid within the stomach and subsequently coating the intestinal lining. FIG. 1B is a drawing indicating the mucoadhesive binding of the compound to the proximal gastrointestinal tract to lower and delay glucose uptake.

FIGS. 1C and 1D are schematics comparing the limitations of existing approaches to reducing nutrient absorption to the advantages of the present intestinal barrier forming compound.

FIG. 3A is a schematic representation of an integrative permeation test. FIG. 3B is a graph showing the effective barrier property of sucralfate. FIG. 3C is a graph depicting correlation of solution viscosity and integrative barrier property. FIG. 3D is a graph of viscosity and mass-normalized barrier property. FIG. 3E is a graph showing viscosity and material attachment on mucin-coated membrane after vertical tilting. FIG. 3F is a graph showing barrier properties and material adhesion of methylcellulose with different molecular weights. FIG. 3G a line graph depicting the integrative barrier function kinetics of sucralfate. FIG. 3H is a graph showing dry weight loss over time of sucralfate, respectively.

FIGS. 4A-4C are a curve fitting showing the viscosity and intrinsic permeation of sucralfate, a graph depicting the integrative barrier function of sucralfate, and a diagram of the reduced thickness of the dense sucralfate barrier layer in acid, respectively.

FIGS. 6A-6F show the properties of the Acidified Sucralfate Paste (ASP). FIG. 6A is a depiction of the fabrication of a sucralfate-based low aluminum releasing Acidified Sucralfate Paste (ASP) that possesses significant barrier function to nutrients. FIG. 6B is a bar graph indicating the relative release of aluminum from sucralfate as a function of acid concentration.

FIG. 6C is a bar graph showing the barrier properties of ASP pastes in the presence of varying acid concentrations, FIG. 6D is a graph depicting the stability of the ASP pastes in simulated stomach acid. FIG. 6E is a graph showing the aluminum/sulfate content ratio remaining in the paste. FIG. 6F is a profile showing the representative dynamic viscosities of the ASP pastes as a function of acid concentration, respectively.

FIGS. 8A-8G show the barrier function and characteristics of the sucralfate based microparticulate composition containing phosphate ions and crosslinking humectant. FIG. 8A is a graph of the barrier function of ASP-PC with the particle stabilizer phosphate and the crosslinking humectant carrageenan. FIG. 8B is a scanning electron microscopy image of ASP particles stabilized with phosphate buffer. FIG. 8C is a size distribution of the particles. FIG. 8D is a bar graph depicting the barrier changes of ASP-P and ASP-PC particles following lyophilization. FIG. 8E is a graph showing the viscosity change of pastes in acid from wet (non-lyophilized) to dry of ASP-PC particles. FIG. 8F is a graph showing the viscosity change of pastes in acid from wet (non-lyophilized) to dry of ASP-P particles. FIG. 8G is a graph showing the shear resistance of ASP-PC and ASP paste in simulated stomach acid.

FIG. 9A is a picture of ASP paste incorporated with sulfate modified and non-sulfate modified fluorescent latex beads. FIG. 9B is a set of bar graphs showing the incorporation of sulfated and non-sulfated fluorescent beads into the paste during the particle fabrication and paste re-formulation process. FIG. 9C is a set of fluorescent images of ASP paste formulated with red fluorescent sulfate-modified latex beads, ASP-P formulated with the red fluorescent sulfate-modified beads, and re-hydrated paste of ASP-P incorporated with the red fluorescent sulfate-modified beads in pH 1.0 simulated stomach acid showing stable incorporation of sulfate-containing substances in ASP during the fabrication process and re-hydration in stomach.

FIG. 11A is a timeline for the protocol for the OGTT for ASP-PC in a full stomach. FIG. 11B is a line graph depicting the postprandial blood glucose response of 5 hour-fasted rats and FIG. 11C is a bar graph showing the area under the curve (AUC) of the data from experiments performed on a full stomach. FIG. 11D is a timeline for the protocol for the OGTT for ASP-PC in an empty stomach. FIG. 11E is a graph depicting the postprandial blood glucose response of 15 hour-fasted rats and FIG. 11F is a bar graph showing the AUC of the data from experiments performed on an empty stomach. FIG. 11G is a timeline for the protocol for the OGTT for saline or native sucralfate in an empty stomach. FIG. 11H is a graph depicting the postprandial blood glucose response of saline or sucralfate-fed rats and FIG. 11I is a bar graph showing the AUC of the data from experiments performed on a full stomach, respectively.

FIG. 12A is a set of four fluorescent images showing the quinine hemisulfate-stained sections of the duodenum (left panels) and jejunum (right panels) from rats administered either ASP-PC (top panels) or saline (bottom panels). FIG. 12B is a graph showing the mean fluorescence intensity of quinine hemisulfate-stained sections of the duodenum and jejunum after oral administration of ASP-PC (following subtraction of the fluorescence of control samples from similar rats administered saline). Statistical significance was analyzed using unpaired Student t-tests with saline-treated segments as controls.

DETAILED DESCRIPTION

Figure 1A:
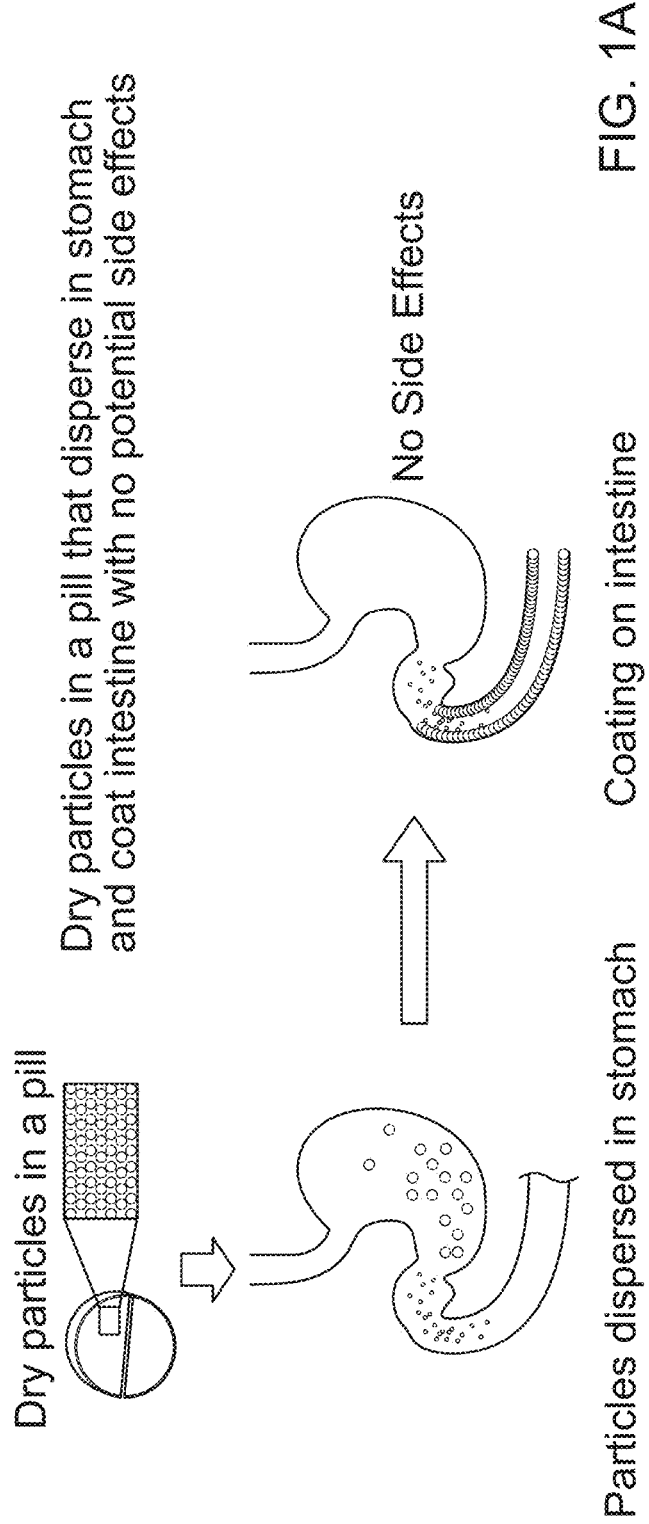
FIGS. 1A-1D are schematics depicting the concept for coating the proximal intestine with an orally administered formulation of a sucralfate-based composition.
Figure 1B:
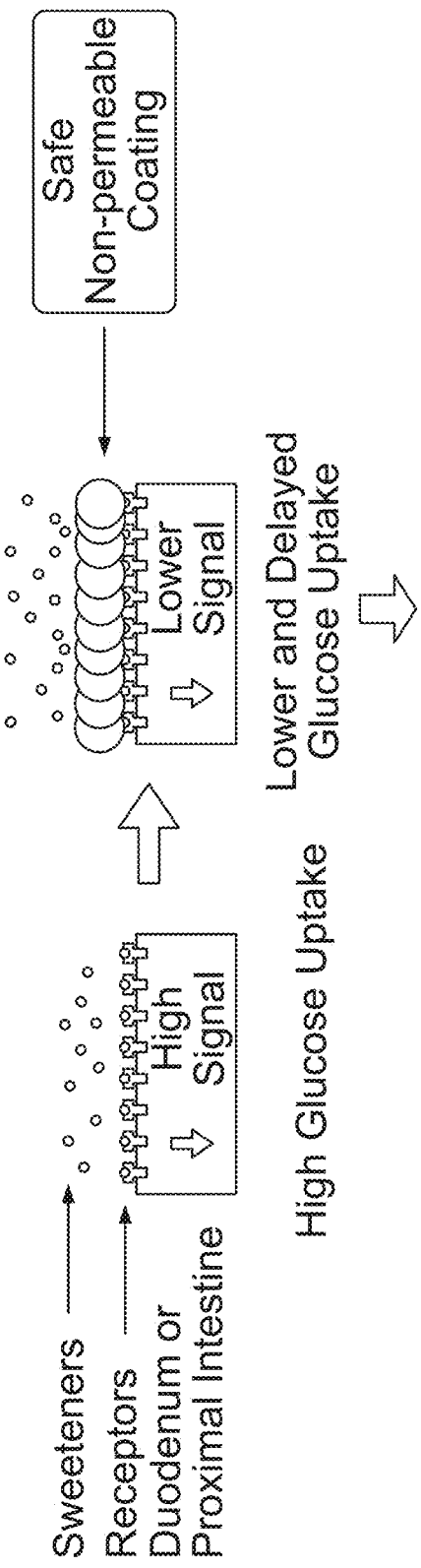

The present disclosure describes methods of altering nutrient exposure via coating of the luminal surface of portions of the GI tract (e.g., proximal GI tract) including the proximal intestine with an orally administered mucoadhesive composition, e.g., a particulate, e.g., microparticulate, formulation, or a liquid formulation (FIG. 1). These compositions are made of particles that include aluminum crosslinked sulfated agents, such as sucralfate, and a particle stabilizer cross-linked together with a crosslinking humectant. Through an in vitro screening process, sucralfate, an FDA-approved drug for stomach and duodenal ulcers that gels into a mucoadhesive paste in the stomach when orally administered, was identified and made into a novel, advantageous formulation. Sucralfate exhibits an effective barrier property to glucose absorption in vitro; however, a significant quantity of sucralfate is liberated during gelation, and thus not available for subsequent coating. Furthermore, during the initial gelation process, aluminum is released from the sucralfate molecule. This released aluminum can potentially accumulate in tissue overtime with repeated exposures, which is undesirable and specifically contraindicated in patients with renal insufficiency. Hence, a sucralfate-based composition was engineered to improve the efficacy of therapy by maximizing the amount of sucralfate available for luminal coating of the gut and simultaneously minimizing the potential side effects by reducing the amount of aluminum content released into the system.

General Methodology

The novel aluminum-crosslinked sulfated agent-based, e.g., sucralfate-based, compositions are inert, non-absorbable microparticulates in the form of dried particulates or suspensions that can temporarily coat the luminal lining of the digestive track and modulate nutrient contact and/or absorption of ingested nutrients through the intestinal lining and thus keep those blocked nutrients from entering into the blood stream or having other systemic effects. The examples below demonstrate that the administration of the new microparticulate compositions described herein provide an effective barrier to glucose absorption in the proximal gastrointestinal tract, to thereby lower postprandial blood glucose concentration. Thus, the new compounds and methods can be useful to treat disorders in which one desires to reduce the absorption of one or more nutrients into the body. For example, management of type II diabetes requires an altered diet, often in addition to a drug or insulin-based therapy. Similarly, controlling various forms of obesity require regulation of food intake together, often with drug therapy or surgical approaches including bariatric surgery. The sucralfate based microparticulate composition described herein reduces nutrient passage from the intestinal lumen to the blood stream through the intestinal lining. For example, inhibition or delayed inhibition of nutrient absorption can mean inhibiting glucose absorption.

The microparticulate compositions described herein are prepared in a manner to reduce the presence of metallic ions (i.e. aluminum ion) in the compositions to thereby reduce the release of aluminum from the sucralfate based microparticulate composition in the presence of acid (i.e., stomach acid), in turn, reducing the potential side effects from excess aluminum in the bloodstream.

Microparticulate Compositions and Methods of Making the Compositions

The aluminum-crosslinked sulfated agent-based, e.g., sucralfate-based or LuCl-based, compositions include or consist of a polymer, a particle stabilizer, e.g., an ion such as a phosphate ion, and a crosslinking humectant. The ions within the microparticulate composition serve as particle stabilizers, because they can surround the individual polymer structures of sucralfate to reduce their tendency to coalesce in the presence of acid. In general, various particle stabilizers can be used, including pectin, carrageenan, chitosan, cellulose derivatives, gellan gum, alginate, gum karaya, dextran, pullulan, polyethylene glycol (PEG), polyvinyl alcohol (PVA), beeswax, sodium borate, stearic acid, carbomer, cetyl alcohol, propylene glycol, polysorbate, lecithin, glyceryl monostearate, acetic esters of fatty acid, lactic esters of fatty acid, citric esters of fatty acid, tartaric esters of fatty acid, acetyltartaric esters of fatty acid, sucroglycerides, polyglycerol esters of fatty acid, propane-2,3-diol esters of fatty acid, sodium stearoyl-2-lactylate, calcium stearoyl-2-lactylate, stearyl tartate, and castor oil derivatives. The particle stabilizer can be either positively or negatively charged.

The resulting non-sticky, dry form is then infused with a crosslinking humectant to allow the particle to be in the form of a non-brittle aggregate. This results in the overall composition having the characteristics of a sticky paste when in the present of acid (i.e., stomach acid).

Figure 2B:
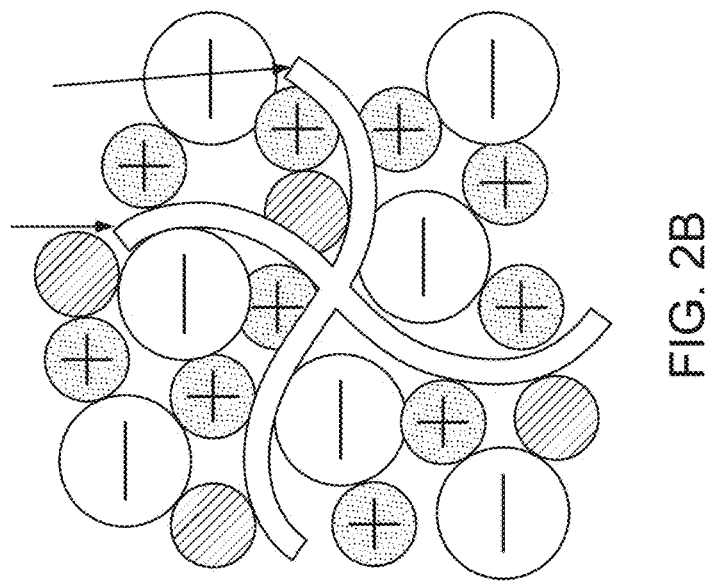
FIGS. 2A and 2B are schematics that indicate the chemical structure of sucralfate and the "sticky paste" fabrication of sucralfate with phosphate ions present as a particle stabilizer and carrageenan as a crosslinking humectant, forming an Acidified Sucralfate Paste Particle (ASP-PC), respectively. The arrows point to the crosslinking humectant.
Figure 2A:
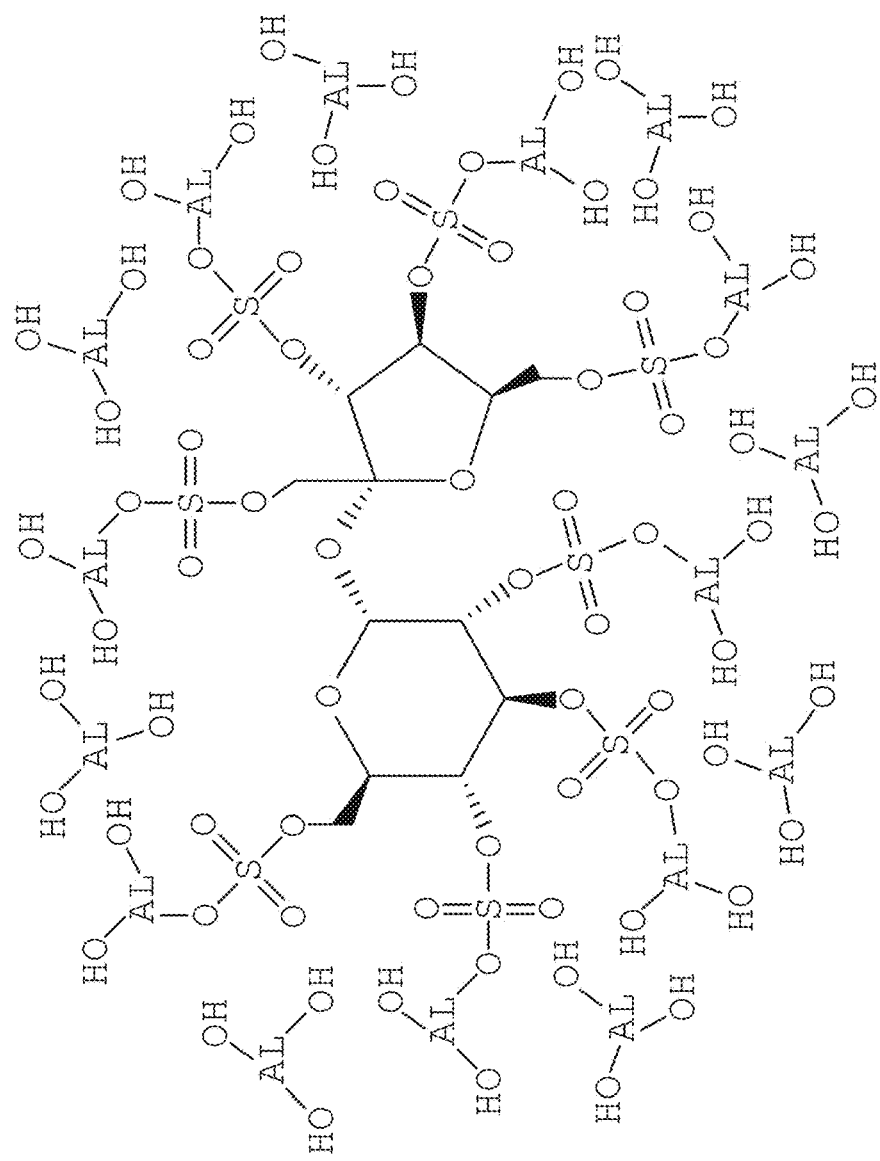
Figure 3A:
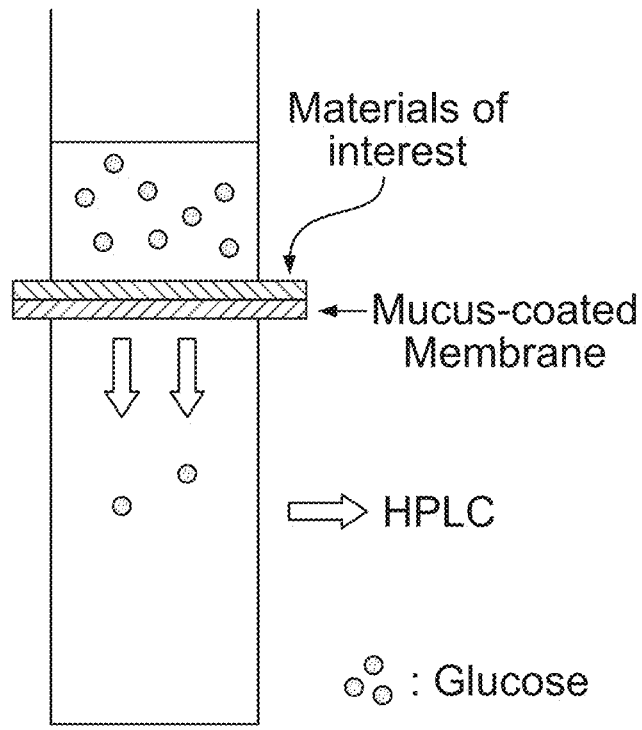
FIGS. 3A-3H show data regarding the barrier function of sucralfate.
Figure 3B:
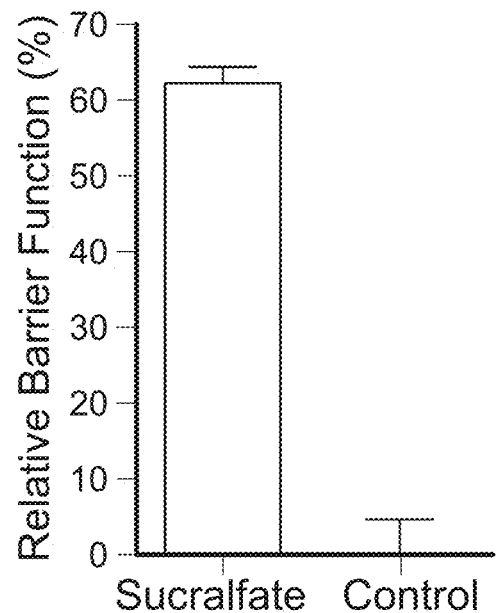
Figure 3C:
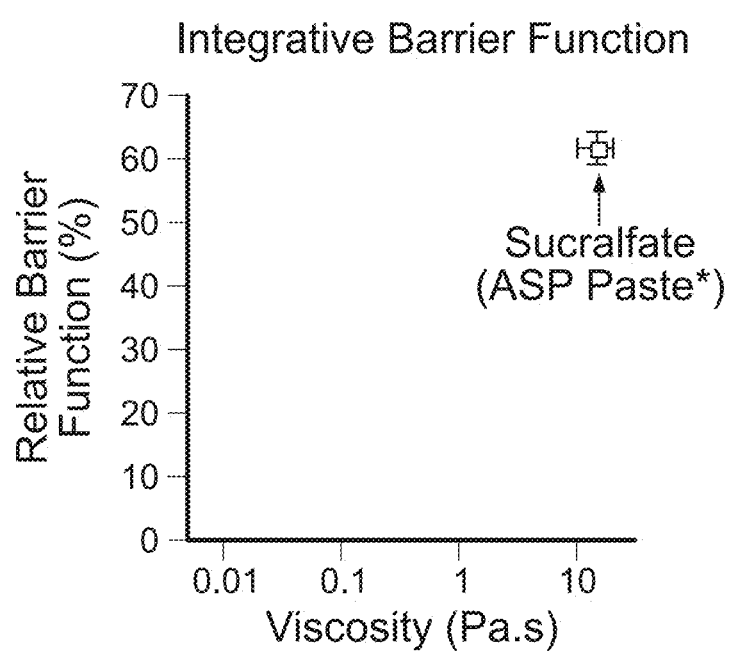
Figure 3D:
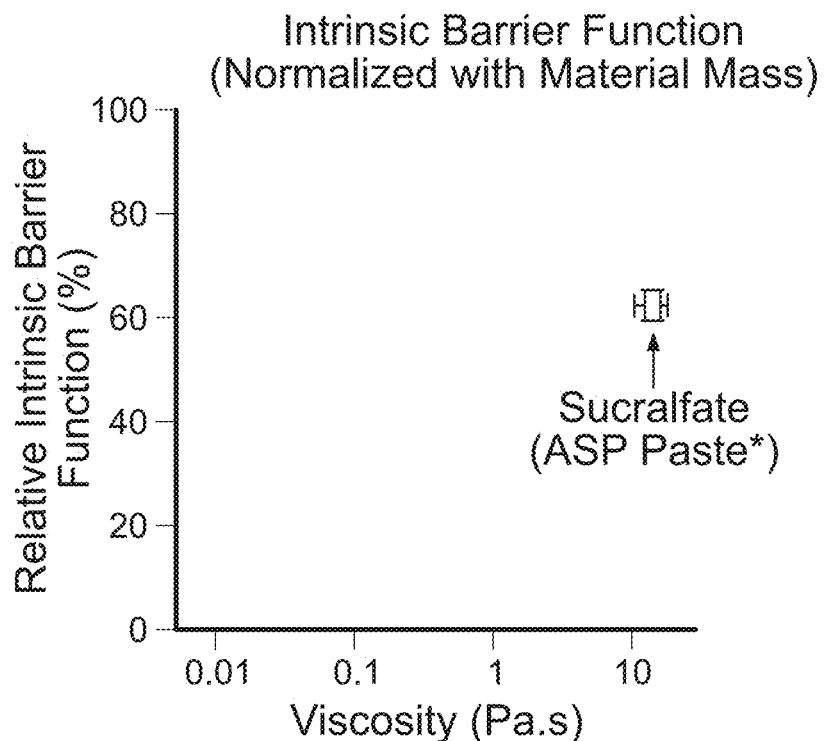
Figure 3E:
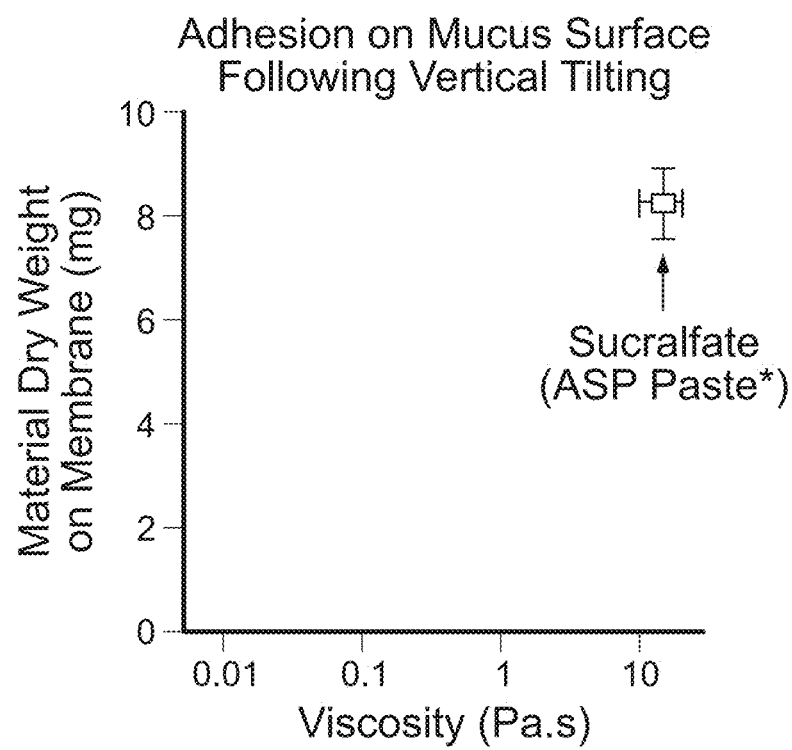
Figure 3F:
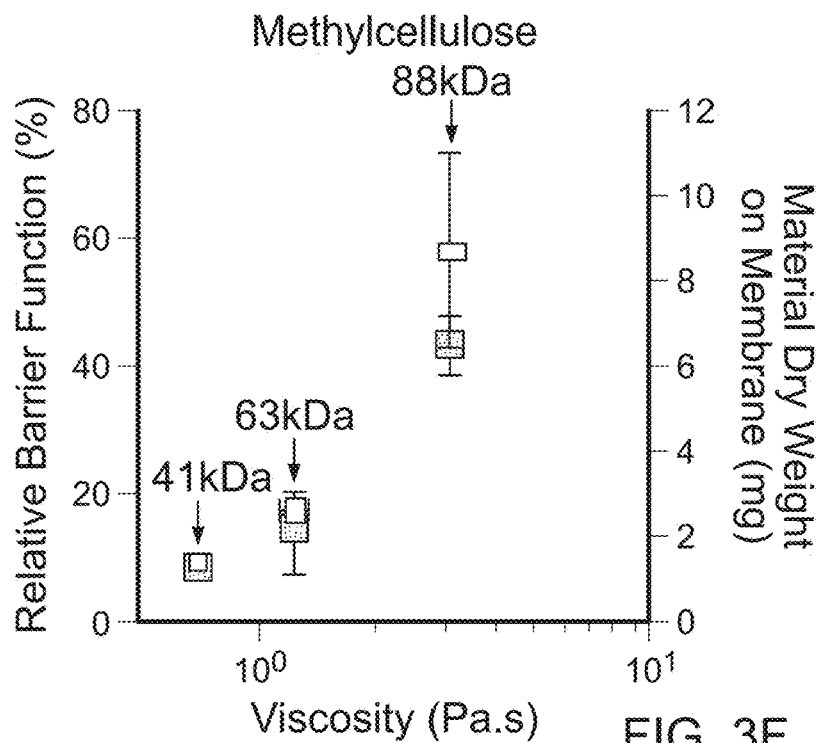
Figure 3G:
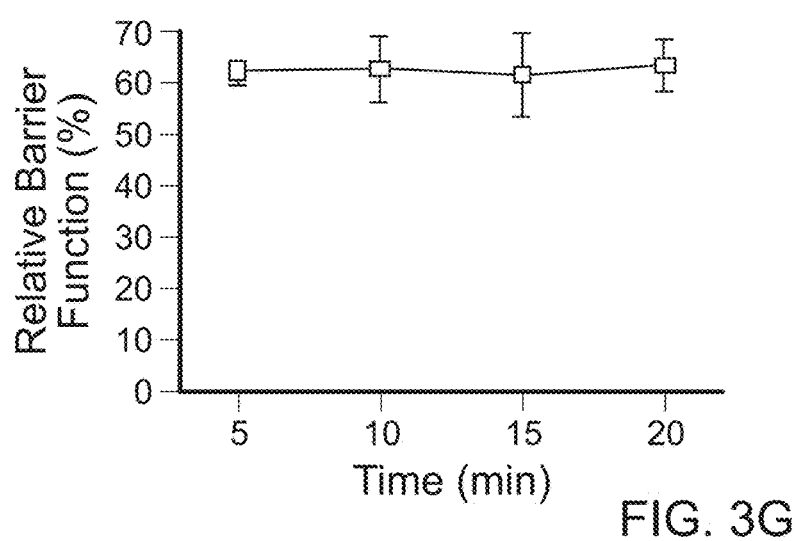
Figure 3H:
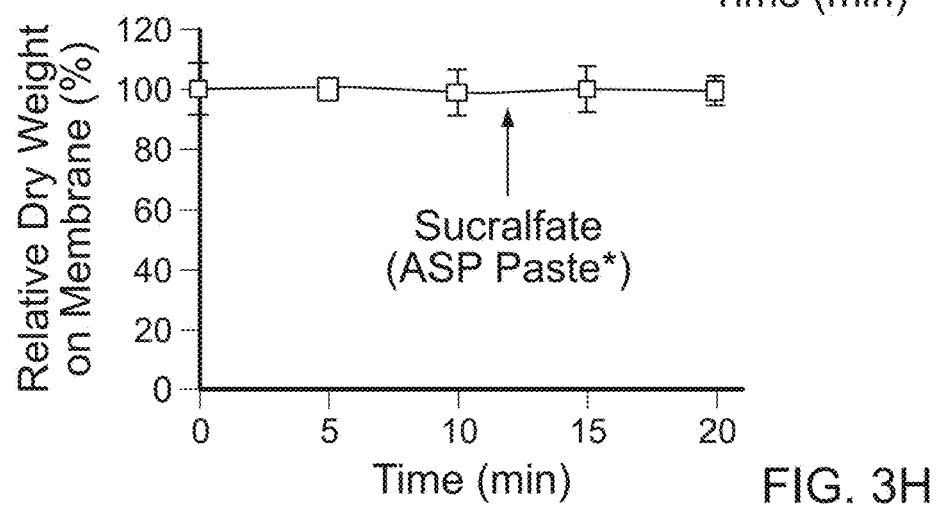

Sucralfate is a sucrose octasulfate-aluminum complex that is an FDA-approved, orally administrated drug indicated for the treatment of active gastric and duodenal ulcers (FIG. 2A). The viscosity of sucralfate is a key determinant of its barrier performance. When exposed to acid (i.e., stomach acid), sucralfate powder itself forms a sticky paste that physically coats the luminal surface of the stomach and duodenum to thicken the protective mucosal layer via a strong mucoadhesive interaction with gastric and duodenal mucus (S. Higo et al; Pharm. Res. 21, 413-419 (2004); Tasman-Jones and Morrison, Am. J. Med., 86, 5-9 (1989); Slomiany et al., Am. J. of Med., 91, 30-36, 1991).

However, the sucralfate molecule contains aluminum. When sucralfate reacts with stomach acid to form a sticky paste, aluminum is released from the polymer. Sucralfate exhibits a low aluminum toxicity profile for the treatment of ulcers because sucralfate therapy is typically administered for short periods for this indication. Hence, one hurdle for the use of sucralfate for the treatment of T2DM is potential excessive aluminum absorption, particularly due to the fact that a prolonged, repeated dosing required for T2DM therapy, leading to long-term aluminum exposure. Further, 25-40% of diabetic patients suffer from chronic renal impairment and hence, may be increasingly susceptible to potential side effects due to the aluminum release from sucralfate. Unlike patients with normal renal function who can adequately excrete the aluminum and hence only retain a limited quantity, patients with CRI can have an impaired excretion of aluminum that could limit the long-term use of sucralfate for T2DM patients (J. P. New et al., Diabetic Medicine, 24, 364-369; Eberhard, Ritz et al., New Engl. J. Med.,341, 1127-1133(1999)). It is essential to ensure that transient nutrient barrier coatings which are to be administered over prolonged periods of time release little to no toxic components such as aluminum. Reducing the exposure of aluminum to a T2DM patient would increase the safety profile of this therapy for clinical translation of sucralfate as an intestinal barrier in patients.

While sucralfate has been tested, other sulfated materials can also be used. For example, sulfated materials including, but not limited to, sulfated dextran, sulfated dextrin, sulfated amylopectin, sulfated amylose, sulfated cellulose, carrageenan, chondroitin sulfate, glucose sulfate, sucrose sulfate, and raffinose sulfate, can be used to create the compositions described herein.

A dry sucralfate-based microparticulate that has the ability to be hydrated was fabricated to replicate the gastrointestinal barrier effect of sucralfate alone. The formulation, however, boasts a decreased release of aluminum compared with that which normally occurs during the sucralfate gelling process in the stomach. It also simultaneously maximizes the amount of material available for coating. The novel formulation requires sucralfate being initially exposed to acid to promote the majority of aluminum release during the production of a sucralfate-based microparticulate. It also utilizes a particle stabilizer to create a non-sticky particle and a crosslinking humectant to create a non-brittle, dry aggregate that can be re-hydrated.

Sucralfate was initially treated with acid to release aluminum from the sucralfate molecule. Following this treatment with acid, sucralfate was in a liquid state. The water content of the formula reduces the amount of material available for coating and presents challenges for specific volumetric dosing. It also creates issues regarding microbial stability and sterilization. To circumvent these issues, the paste was engineered into a dried non-mucoadhesive formulation that could be lyophilized and rehydrated at a later time in acid to form a mucoadhesive paste with an effective nutrient barrier property. The particulate form of sucralfate enables increased flexibility for formulating.

Acid-treated sucralfate particles coalesce rapidly. Hence, to achieve a stable suspension of acid-treated sucralfate particles, a film-forming material that could coat the surface of sucralfate particles was utilized. Phosphate ions were used as a particle stabilizer to create a stable formulation of acid treated sucralfate. The binding of phosphate ions acts as a temporary particle stabilizer allowing the 'low aluminum releasing acidified sucralfate paste' (ASP) to exist as a non-sticky particle (ASP-P). This dry ASP-P forms a brittle aggregate in the presence of acid thereby reducing its efficacy as an intestinal coating therapy. Thus, we developed a dry, non-brittle formulation in which we cross-linked (e.g., through ionic interaction) a crosslinking humectant, i-carrageenan, to the APS-P. When in the presence of acid, this resulting formulation, ASP-P Carrageenan (ASP-PC), forms a sticky paste. This sticky paste is a mucoadhesive and will thus coat the lining of the intestine for a prolonged period of time (FIG. 2B).

Of course, other crosslinking humectants than carrageenan can also be used in the methods described herein. For example, crosslinking humectants can include, but are not limited to, propylene glycol, 1,2,6-hexanetriol, butylene glycol, dipropylene glycol, hexylene glycol, glycerin, triethylene glycol, erythritol capryl glycol, phytantriol, hexanediol beeswax, hexanetriol beeswax, panthenol, sodium pyrollidone carboxylic acid, hyaluronic acid, inositol, glycogen, sorbitol, polyglyceryl sorbitol, glucose, fructose, xylitol, elastin, collagen, silk, keratin, isoceteth, isolaureth, laneth, laureth, steareth, polyethylene glycol, silicon copolymers, ammonium lactate, glyceryl triacetate, hydrolyzed collagen, hydrolyzed elastin, hydrolyzed keratin, hydrolyzed silk, lactic acid, manitol, panthenol, polydextrose, propylene glycerol, quilaia, urea, and betaine. Thus, some of the same materials can be used as particle stabilizers or crosslinking humectants, but in many implementations, the particle stabilizer and the crosslinking humectant are different materials.

The duration of sucralfate in the GI tract is about 2-6 hours followed by excretion via feces. ASP-PC can be expected to last about the same length of time, but the duration can be tailored to be shorter or longer based on viscosity and charge for specific compositions.

In some examples, the compositions provided herein can further include a powdered acid. Non-limiting examples of powdered acids include sodium citrate, ascorbic acid, boric acid, hydrochloric acid, and ascetic acid. In some examples, the compositions provided herein can include a liquid acid (e.g., LuCl). In some examples, the particles within any of the compositions described herein are encapsulated by an enteric coating. For example, the coating can be comprised of one or more of gelatin, hydroxypropyl methylcellulose (HPMC), Eudragit®, and Acryl-EZE®. In some embodiments, the composition is a capsule containing the particles described herein.

All of the microparticulate compositions described herein can be prepared by methods well known in the art and the reagents of which can be readily obtained from a commercial source. For example, sucralfate can be obtained from a commercial source such as Sigma-Aldrich (St. Louis, Mich.). The compounds described herein may contain a polymer which includes aluminum in its structure. In addition, the compounds described may contain an ion and a polymer which could coat the surface of the aluminum-containing polymer.

The microparticulate compositions described herein are not absorbed by the body of the patient to whom they are administered. A plurality of the resulting dry microparticles is packaged into a pill form. In the presence of stomach acid, the particles are separated and dispersed. The particles are not processed and continue to move into the proximal intestine. In the presence of acid, the particles are mucoadhesive and they subsequently coat the lining of the intestine. The microparticles adhere to the proximal gastrointestinal tract forming a temporary, safe, non-permeable coating. The microparticles are not absorbed through the intestinal lining. The coating delays and/or reduces/inhibits absorption of nutrients, including glucose and potentially fats, carbohydrates, and proteins, which may be blocked as well by the physical barrier formation from the sucralfate-based microparticulate composition.

In general, the microparticulate compositions form a mucoadhesive barrier layer in the duodenum or proximal intestine following food intake, but in some instances may also form such a barrier layer in the stomach or other portions of the GI tract, which may contribute to the therapeutic effects of the compositions.

Any of the compositions provided herein can be a food substance (e.g., a bar or shake) or additive (e.g., a salt). Additional examples of food substances or additives are known in the art.

Over time, the sucralfate-based coating is released from the lining of the intestine, degraded and excreted.

Methods of Using the Microparticulate Compositions

The aluminum-crosslinked sulfated agent-based, e.g., sucralfate-based, microparticulate compositions can be used to create an intestinal coating to inhibit nutrient absorption as a therapy or as an add-on therapy for patients with disorders that require reduction of ingested nutrients. T2DM patients exhibit increased blood glucose after ingesting glucose via routine food intake due to inadequate insulin production and regulation from the pancreas. Increased blood glucose levels lead to the classical symptoms of polyuria, polydipsia, and polyphagia. However, if left untreated, T2DM can lead to serious complications including ketoacidosis, hyperosmolar coma, cardiovascular disease, chronic renal failure, and retinopathy. Maintaining a healthy weight as a T2DM patient is an important life style factor to avoid increased severity of diabetes, increased complications, or even death. Hence, the use of a sucralfate-crosslinking humectant microparticulate by a T2DM patient would have dual benefits: reduction of glucose absorption, as well as reduction of absorption of other nutrients resulting in weight loss (e.g., fats and carbohydrates), and weight loss.

Figure 1D:
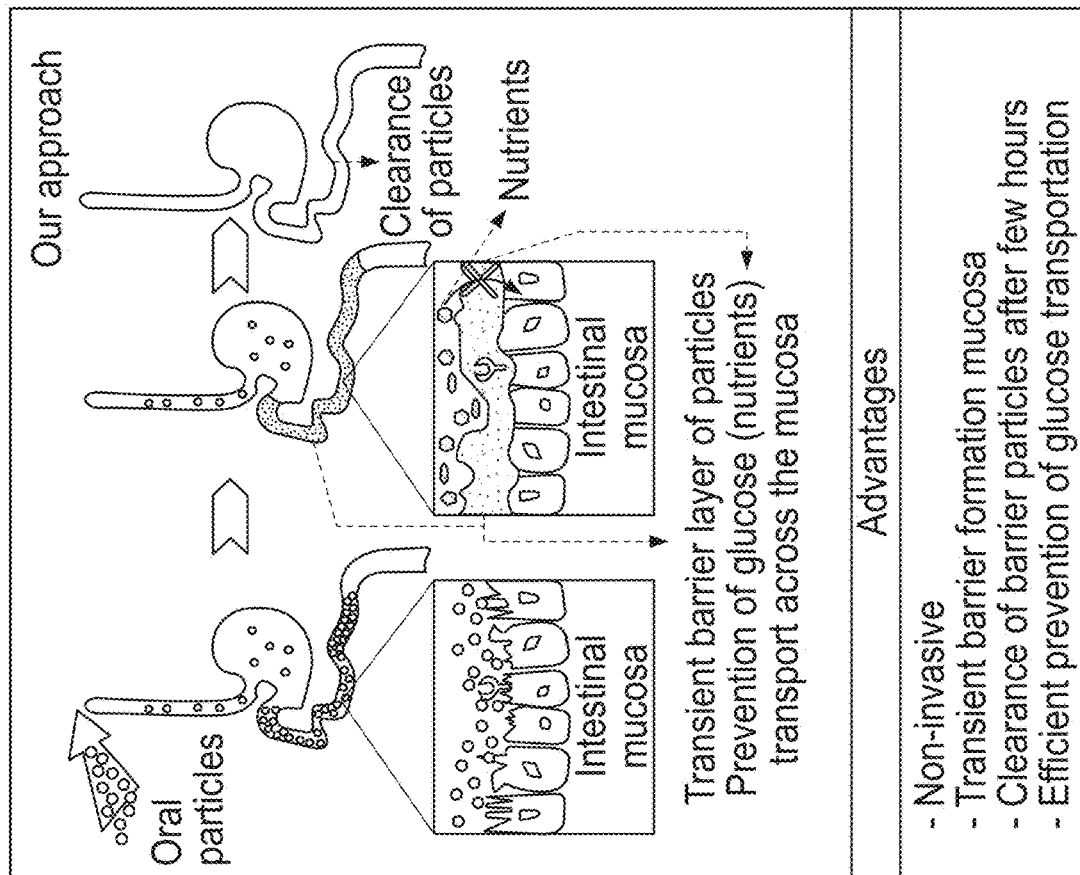
Figure 1C:
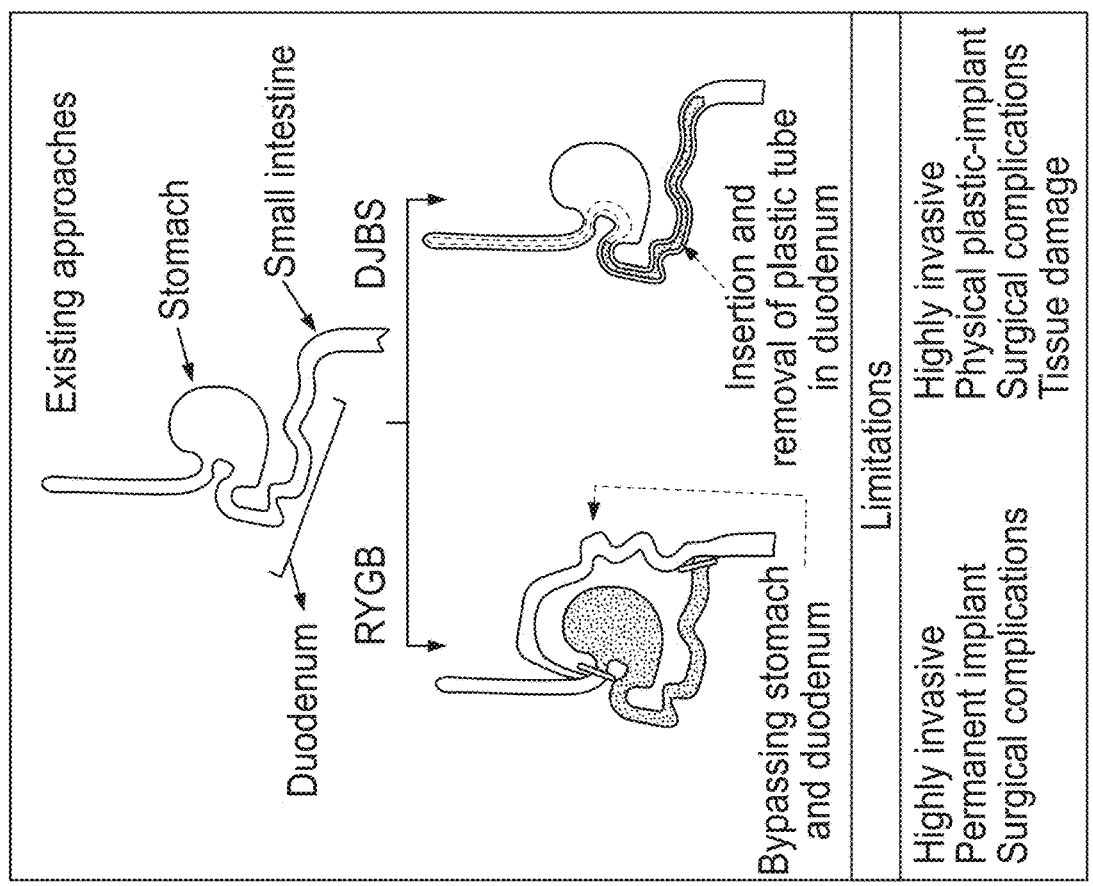

As shown in FIGS. 1C and 1D, the decreased, or in some cases delayed, uptake of, for example glucose, could be a treatment for type II diabetes. In effect, it can lessen the dose needed for diabetes treatments including insulin, metformin, or sulfonylureas. The presence of the barrier particles resulting from the novel formulation forming a lining along the proximal gastrointestinal tract can also modulate (e.g., decrease) the absorption of nutrients as the digested nutrients move through the intestine. The presence of the barrier particles creates a decreased surface area of the intestinal lining available to be in contact with digested nutrients and hence results in decreased or delayed absorption of such nutrients. The sucralfate based microparticulate compositions described herein are a potential therapy or add-on therapy for obesity, weight control, insulin resistance, hyperlipidemia, hypertension, and T2DM.

In other implementations, the new compositions can be used to carry other materials, such as drugs or anti-microbials. The release of the materials from the barrier layer can be controlled and can occur for an extended time period, yet is temporary. In another example, one can combine iodine, silver ions, and/or a chlorine-containing substance with the new compositions for attachment and slow release to inhibit the growth and/or proliferation of various microorganisms on surfaces, e.g., in the GI tract.

In any of the methods described herein, the subject is administered a dose of any of the compositions described herein when their stomach is substantially empty of food. For example, in any of the methods described herein the subject is administered a dose of any of the compositions described herein before eating (e.g., before eating a meal). The subject can be administered any of the compositions described herein between about 2 hours and about 1 minute (e.g., between 1.8 hours and 5 minutes, between 1.5 hours and 10 minutes, between 1.3 hours and 15 minutes, between 1.0 hour and 20 minutes, between 50 minutes and 25 minutes, or between 40 minutes and 25 minutes) before eating (e.g., before eating a meal). In other embodiments, the subject is administered any of the compositions described herein at substantially the same time as eating (e.g., while eating). The subject can be administered, e.g., one, two, three, four, five, six, or seven doses of any of the compositions described herein a day (e.g., over a total period of at least 1 month, at least 6 weeks, at least 2 months, at least 10 weeks, or at least 3 months). Some examples of the methods provided herein further include monitoring a subject's blood glucose levels and/or weight (e.g., before and after administration (e.g., repeated administration) of any of the compositions provided herein.

Pharmaceutical Formulations and Dosage Forms

Also within the scope of this disclosure are pharmaceutical compositions containing at least one compound described herein and a pharmaceutically acceptable carrier. Further, this disclosure covers methods of administering an effective amount of the compounds described herein, e.g., in a pharmaceutical composition, to a patient having T2DB or obesity, e.g., as described herein. "An effective amount" or "an amount effective" refers to the amount of a compound that is required to form a barrier on the lining of a portion or portions of the GI tract to confer a therapeutic effect on the treated patient. Effective doses will vary, as recognized by those skilled in the art, depending on the types of diseases treated, route of administration, excipient usage, and the possibility of co-usage with other therapeutic treatment.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Exemplary doses can range from about 5 g/day for an adult to a maximum dose of sucralfate of about 8 g/day for adult (~114 mg/kg for 70 kg adult). For the new microparticulate compositions the dosages can be higher, from about 25 to about 50 g/day, with the potential to be administered in a liquid form, because of the significantly lower level of aluminum in the new compositions compared to sucralfate alone. In other examples, the dose can be between about 1 g/day to about 8 g/day (e.g., between 2 g/day to about 7 g/day).

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound described above. Examples of other carriers include colloidal silicon oxide, magnesium stearate, cellulose, sodium lauryl sulfate, and D&C Yellow #10.

The therapeutic compounds can also be prepared with carriers that will protect the therapeutic compounds against rapid elimination from the body, such as a controlled release formulation. Biodegradable, biocompatible polymers can be used, such as ethylene vinyl acetate, polyanhydrides, polyglycolic acid, collagen, polyorthoesters, and polylactic acid. The new compositions can be incorporated into controlled release formulations to modulate cranio-caudal distribution and retention time. Examples using such formulations are included below (examples 6 and 7). In addition, these formulations can be used to control the duration of the desired effects, for example, by altering the charge and/or viscosity of the overall formulation. In addition, the new compositions can be mixed with, e.g., "doped" with, additional drugs and can then be used as a drug delivery system.

Such formulations can be prepared using standard techniques, or obtained commercially, e.g., from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

Some compositions and pharmaceutical compositions can include a dry acid salt or a liquid acid salt (e.g., any of the exemplary dry acid salts or liquid acid salts described herein or known in the art). Such compositions and pharmaceutical compositions can be wetted with an aqueous solution before being administered to a subject or patient (e.g., administered to the small intestine of a subject).

The pharmaceutical compositions can be included in a container, pack, or dispenser together with instructions for administration.

Methods of formulating suitable pharmaceutical compositions are known in the art, see, e.g., the books in the series Drugs and the Pharmaceutical Sciences: a Series of Textbooks and Monographs (Dekker, N.Y.).

The compounds described herein can be preliminarily screened for their efficacy in treating above-described diseases by the whole-organism screening methods described herein and then confirmed by additional animal experiments and clinic trials. Other screening methods will also be apparent to those of ordinary skill in the art.

EXAMPLES

The invention described herein is a novel formulation of a polymer that can form a mucoadhesive layer on the intestinal wall, and hence act as a barrier to the absorption of digested nutrients traveling through the digestive tract. The invention is further described in the following examples, which do not limit the scope of the invention described in the claims.

Example 1

Identifying Sucralfate as an Intestinal Coating Material Methods

A mucin-coated membrane was prepared to mimic the mucus surface of the intestine to examine barrier properties of sucralfate in vitro. Specifically, a cellulose nitrate membrane (pore size: 0.2 μm, Whatman, Germany) was incubated in a 3% w/v porcine stomach mucin (Sigma-Aldrich, USA) solution in Hank's balanced salt solution (HBSS) and gently shaken for 2 hours at room temperature. The membrane was washed with distilled deionized water (DDW, pH 7) to remove the excess mucin solution. The mucin-coated membranes were used within 1 hour following preparation. To measure the thickness of the mucin layer, the mucin-coated membrane was lyophilized and imaged using scanning electron microscope (SEM) and the thickness of randomly selected positions was examined (average mucin layer thickness: ~100 μm).

The nutrient barrier properties of sucralfate were tested by applying 1 milliliter (ml) of a 1% sucralfate suspension in simulated stomach acid (pH 1.0) evenly to a mucin-coated membrane and vertically tilted for 1 minute. To determine the coating efficiency of sucralfate, the material-attached membrane was lyophilized after pre-determined incubation times in simulated stomach acid (pH 1.0) (5 minutes; 10, 15, and 20 minutes for selected materials) followed by dry weight analysis. The dry weight was calculated from dry weights of material-attached membranes and mucin-coated membranes. The material attached to the mucin-coated membrane was mounted in the Franz-cell system and 3 mL of glucose solution (120 g/L) was added and samples were collected from the receiver part of the system after 5 minutes (10, 15 and 20 minutes and up to 3 hours for sucralfate). The permeation test was performed in triplicate. The glucose concentration was measured using high performance liquid chromatography (HPLC, Agilent, USA) with an analytical C18 column (Zorbax Eclipse XDB-C18, Agilent). The flow rate was 1 ml/minute, the eluent was DDW, and the wavelength of UV detector was 195 nm. All results were normalized to a mucin-coated membrane without application of a sucralfate (0% blocked).

The mechanical properties of 1% w/v sucralfate solution in simulated stomach acid was analyzed using a rheometer (AR-G2, TA Instruments) to obtain viscosity measurements. Dynamic viscosity was measured using a 20-mm plate with 200-μm gaps (shear rate: 0.01-100 1/s in log scale, shear rate of 1 1/s was selected to compare viscosity of materials).

Each 1 ml of 1% w/v material solution in simulated stomach acid was filled between two cellulose nitrate membranes with an 8-mm gasket as a spacer (the filter was not tilted here as in the integrated permeation test) in a Franz cell apparatus to exam the inherent permeability of sucralfate. Glucose solution in simulated stomach acid (120 g/L) was added and samples were collected from the receiver part of the system after 30 minutes. The permeated glucose was measured using HPLC as described above.

Results

Sucralfate achieved a highly effective barrier property to glucose permeation and exhibited blocking of the glucose at 62% (FIG. 3). Sucralfate exhibited a very high viscosity, but not the lowest permeability of glucose in the system (FIG. 4A), as was predicted by the Stokes-Einstein relationship. This was likely due to the reduced thickness of the dense sucralfate barrier layer compared to other more gelatinous materials (FIG. 4A). Subsequently, the ability of sucralfate to remain attached to the vertically tiled mucin-coated surfaces showed good adhesion. Sucralfate formed a stable coating on the mucin-coated surface and maintained a substantial barrier effect for several hours (FIGS. 4B and 4C).

Example 2

Making a Sucralfate Particle with Decreased Aluminum Content

Methods

Acid treated sucralfate was developed by reacting 300 milligrams of sucralfate in 3 ml of HCl solution (0.1-0.3 N). The resulting dispersion was stirred vigorously until the powder was agglomerated together into a paste or completely dissolved (usually within 1-2 minutes). The paste was further incubated under ambient conditions for 2 hour. The supernatant was removed and the paste was purified through washing with fresh 0.1 N HCl solutions (3×) and followed by distilled water (3×).

To confirm the pH dependent release of aluminum from sucralfate and ASP, aluminum-release was measured during ASP paste formation. Five hundred mg of sucralfate was added in 10 ml of simulated stomach acid (pH 1.0), HCl solutions (0.1-0.3N) or DDW with vigorous vortexing for 5 minutes followed by a 2 hour incubation. The aluminum content in the supernatants was measured using inductively coupled plasma atomic emission spectroscopy (ICP-AES, ULTIMA-2, Horiba).

To measure additional aluminum release from aluminum-pre-released ASP, formed pastes were washed with DDW, and 500 mg was added to 10 ml of simulated stomach acid. The samples were vortexed for 5 minutes and incubated for 2 hours. The aluminum content in the supernatant solutions was measured using ICP-AES.

To assess mechanical stability and physical properties of ASP, each 500 mg of ASP prepared from HCl solutions (0.1-0.3N) was added to 1 ml of simulated stomach acid (pH 1.0) in 37° C. At time points including 0, 10, 30, 60, 120 and 300 minutes, supernatant was removed to measure the wet weight. The remaining paste was lyophilized to measure the dry weight. The original amount of sucralfate (500 mg) was set as 100%.

Results

Figure 5:
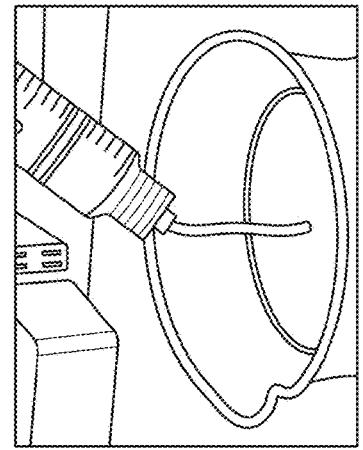
FIG. 5 is a bar graph that illustrates the relative amount of aluminum released from the sucralfate polymer in the presence of acid.

Exposure of sucralfate to increasing concentrations of acid resulted in the increased relative removal of aluminum from the sucralfate molecule (FIG. 5). Although sucralfate exhibits a low toxicity profile for treatment of ulcers, its use is typically necessitated for only a few weeks. One hurdle for the use of sucralfate for treatment of T2DM is potential aluminum absorption and retention in a patient's system, especially following prolonged, repeated dosing leading to long-term aluminum exposure. Elemental analysis using inductively coupled plasma atomic emission spectroscopy (ICP-AES) confirmed that ~9.4% of the original aluminum content was released during the reaction with simulated stomach acid (pH 1.0). To maximize the safety of sucralfate particles for clinical translation, it is essential to ensure that transient nutrient barrier coatings that are administered over the long-term, would not release toxic components such as aluminum.

Figure 6A:
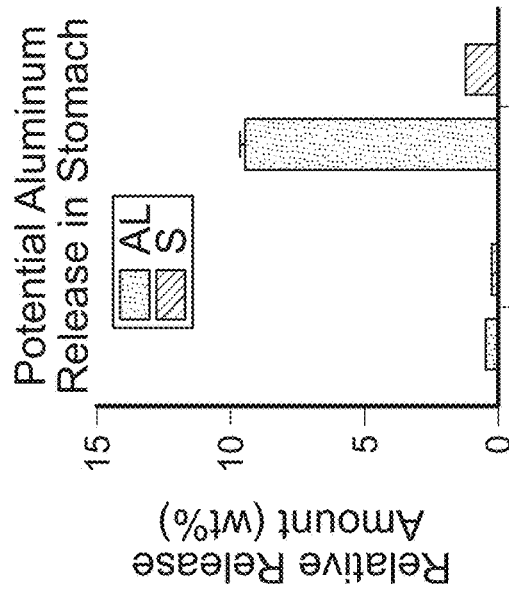
Figure 6A:
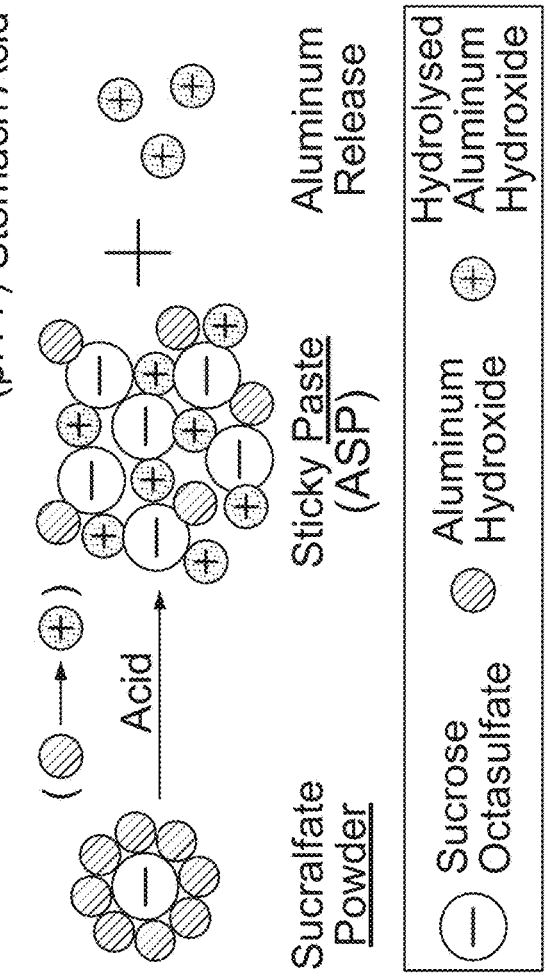

To replicate the intestinal barrier effect of sucralfate with less aluminum release during the gelling process in the stomach, and to maximize the amount of material available for coating, a dry and hydrate-able microparticle paste that does not liberate aluminum in the presence of stomach acid was fabricated. A formulation where sucralfate was initially exposed to acid to promote the majority of aluminum release prior to oral administration was envisioned. As a first step, the amount of aluminum released upon exposure to different concentrations of acid was examined, and subsequent aluminum release following repeated acid exposure. In acidic solutions, the acidified sucralfate is partially hydrolyzed releasing aluminum ions within hydroxylated species (FIG. 6A). Given that the aluminum also acts as a cross-linker to aggregate the sucrose sulfates into insoluble sticky pastes, the sucralfate loses viscosity if the hydrolysis proceeds further. Sucralfate was reacted with 0.1-0.3N HCl solutions in water (pH 0.52-1.00) and according to the acidity of the reaction solution, sucralfate released varying percentage of the total aluminum present (bound) in the composition, ranging from ~9.4% (in 0.1N HCl) to ~44.8% (in 0.3N HCl) (FIG. 6B).

Following the initial exposure, the resultant pastes (acidified sucralfate paste, ASP) showed significantly lower subsequent aluminum release following re-exposure to simulated stomach acid and pH 7.4. PBS (<0.2% of the original content released for a 30 minutes exposure). Importantly, the ASP made in 0.1N HCl exhibited comparable barrier properties to native sucralfate (63% blocking), however the ASPs made in higher concentrations of acid (lower pH) showed limited barrier properties (18% blocking for 0.2N HCl and 17% blocking for 0.3N HCl) (FIG. 6C). The 0.1N HCl ASP showed higher resistance to shear stress, and lower erosion in PBS with gentle shaking compared to 0.2N and 0.3N HCl ASPs (FIG. 6D). Higher acid concentrations likely compromise barrier properties by releasing more aluminum (aluminum/sulfate content ratio remaining in the paste: 1.83, 1.72 and 1.27 for 0.1, 0.2 and 0.3N ASPs) to generate less cross-linked and less viscous pastes (FIGS. 6E and 6F).

Example 3

Making a Humectant-Crosslinked Sucralfate Microparticle

Methods

To fabricate an effective, low aluminum releasing, non-brittle aggregate sucralfate microparticle ASP-P and ASP-PC particles, 500 mg of sucralfate was reacted in 5 ml of 0.1N HCl (for ASP) or 5 ml of 0.01 w/v % ι-carrageenan solution in 0.1N HCl (for ASP-PC), incubated for 2 hour under ambient conditions and washed in DDW three times. Ten milliliters of phosphate buffer (pH 7.4) or phosphate buffered saline (PBS, pH 7.4) was added in the vial containing the paste and vortexed (600 rpm) to provide shear force for 5 minutes. The fabricated particles were extensively washed with double distilled water (DDW) at least 5 times to remove excess buffer. The particles were stored in DDW (wet formulation) or they were lyophilized (dry formulation).

Stabilizing materials i-carrageenan and phosphate buffer (pH 7.4) were used to fabricate stable sucralfate particles. The resultant particles were extensively washed and dispersed in DDW. The final concentration of the particle dispersion was adjusted to 10 mg in 0.9 ml in DDW. The barrier properties of the resultant particles were measured by adding 0.9 ml of particle dispersion and 0.1 ml of 10× simulated stomach acid. Particle size was measured using an automated cell counter equipped with a size analyzer (Cellometer, Nexelom, USA).

Shear resistance of sucralfate paste and ASP-PC was measured to evaluate the enhanced attachment to healthy mucosa. Given that sucralfate liberates ~10% of total mass upon exposure to stomach acid, to directly compare mass normalized effectiveness between wet (not lyophilized) ASP and ASP-PC, 1 ml of 1% sucralfate or 1 ml of 0.9% ASP-PC in simulated stomach acid was applied to mucin-coated cellulose nitrate membranes. The membranes were mounted in a flow chamber (height: 0.01 inch, width: 10 mm). To simulate the luminal flow in the duodenum, simulated stomach acid was infused at a rate of 1.44 cm/s (2.198 ml/minutes). Following 0, 5, 15, 30, and 60 min, each membrane was collected and lyophilized to measure the dry weight. This experiment was performed on 3 separate occasions (n=3).

Results

Figure 7A:
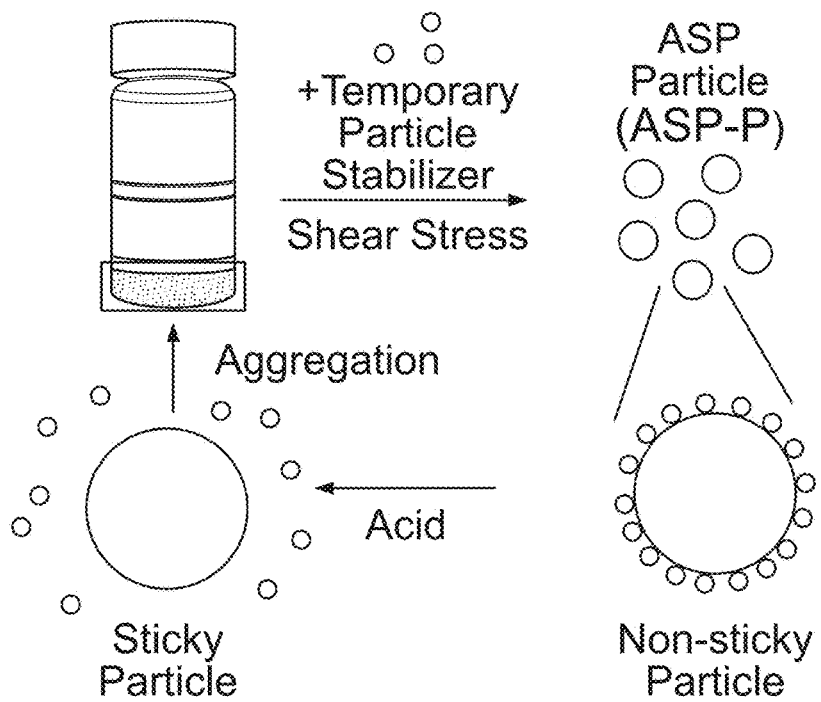
FIGS. 7A and 7B are illustrations of the formulation of the dried microparticulate of low aluminum-releasing ASP paste with a particle stabilizer (ASP-P) and of a humectant cross-linked ASP-P (ASP-PC).
Figure 7B:
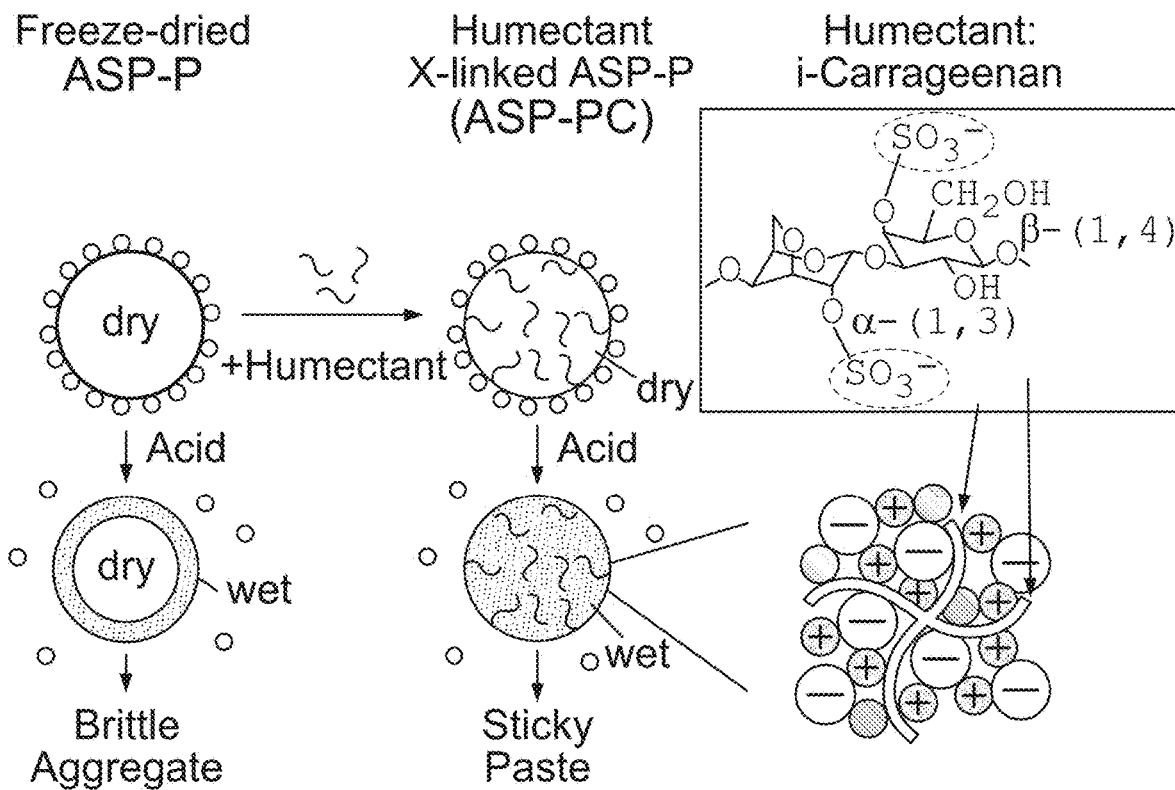
Figure 8E:
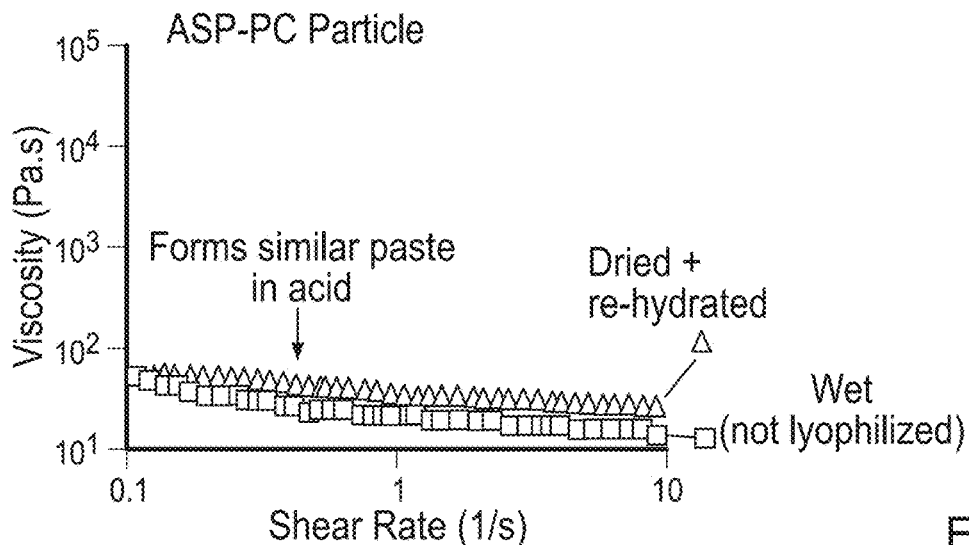

Following treatment of sucralfate with acid (detailed in Example 2), sucralfate was in a liquid state. The water content reduces the amount of material available for coating and presents challenges for specific volumetric dosing. To circumvent this, the paste was engineered into a dried non-mucoadhesive formulation that could readily be lyophilized (FIG. 7A) and be subsequently rehydrated in acid to form a mucoadhesive paste with effective nutrient barrier properties (FIG. 7B). The barrier properties of the sucralfate suspensions were tested using the integrative permeation test (FIG. 8A). Sucralfate stabilized in phosphate buffer (pH 7.4) and subsequently applied to membranes under acidic conditions exhibited a 49% glucose barrier. Stabilized sucralfate particles exhibited a round shape with an average diameter of 15.1±4.3 μm and zeta potential of −11.6±4.3 mV (FIGS. 8B and 8C) and exhibited long-term stability as determined by their unchanged diameter during 2-week incubation in DDW.

However, following lyophilization and rehydration, the phosphate-stabilized particles exhibited extremely poor barrier properties, ~0% blocking (FIG. 8D). This occurred given that the dried particles form a brittle aggregate in simulated stomach acid due to the mal-absorption of water into the particle core. To address this problem, hydrophilic crosslinking humectant molecules of carrageenan were incorporated into the ASP, prior to particle formation (FIG. 7B). To maximize efficacy of hydration, i-carrageenan, a highly sulfated polysaccharide, was selected given its potential to be fully integrated into the sucralfate particles via electrostatic interaction. Carrageenan is an effective stabilizer since it acts as a cross-linker or 'spacer' connecting sucralfate via an aluminum center where the polymer sulfate acts as a substitute for the hydroxyl ligand.

Figure 9A:
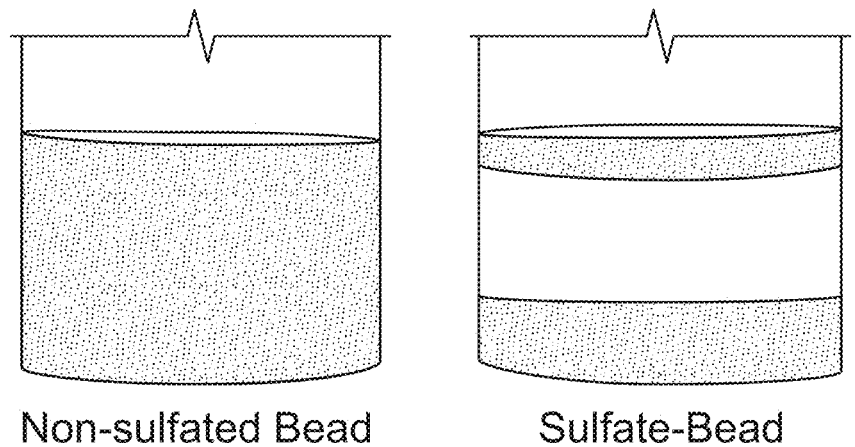
FIGS. 9A-9C depict the incorporation of sulfate-modified latex beads in ASP paste to show incorporation of sulfate-containing substances such as carrageenan.
Figure 9B:
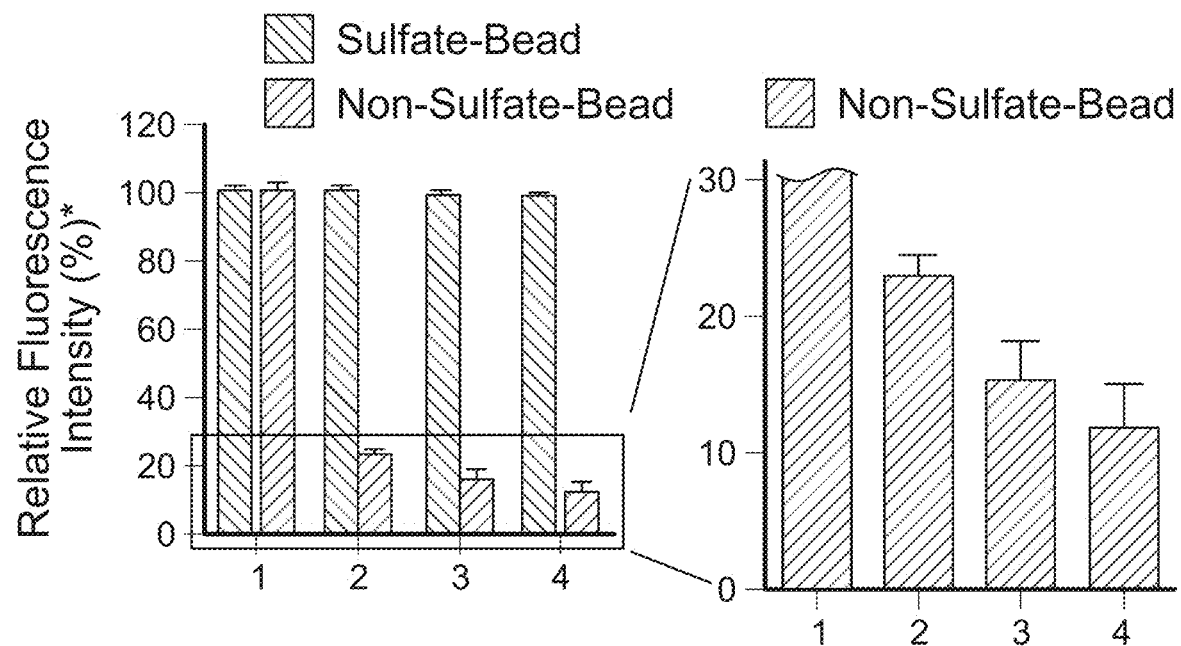
Figure 9C:
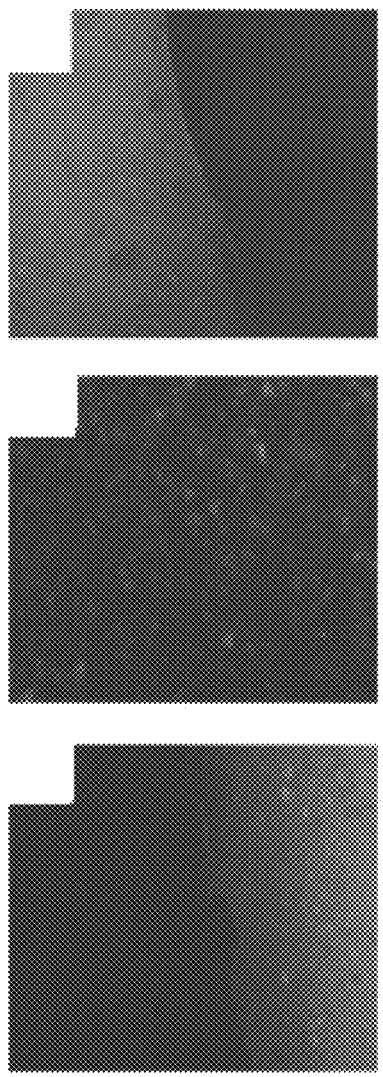

To support the interaction between ASP and sulfate groups, sulfate-modified or non-sulfated-modified fluorescent latex beads (100 nm in diameter) were mixed with sucralfate and acid (0.1N HCl) was added. The sulfated beads fully and stably integrated into the paste and resisted release during lyophilization and re-hydration, however the non-sulfated beads exhibited a low affinity for the sucralfate paste (see FIGS. 9A, 9B, and 9C). Importantly, in the integrative glucose barrier function tests, ASP functionalized with phosphate ions and ι-carrageenan (ASP-PC) that was lyophilized and rehydrated in acid exhibited excellent barrier property (61% blocking) comparable to wet (not lyophilized) ASP-PC (58% blocking), unlike lyophilized carrageenan-free ASP-P particles that was rehydrated in acid and showed a steep decrease in barrier property (0% blocking) (FIG. 8D).

Figure 8F:
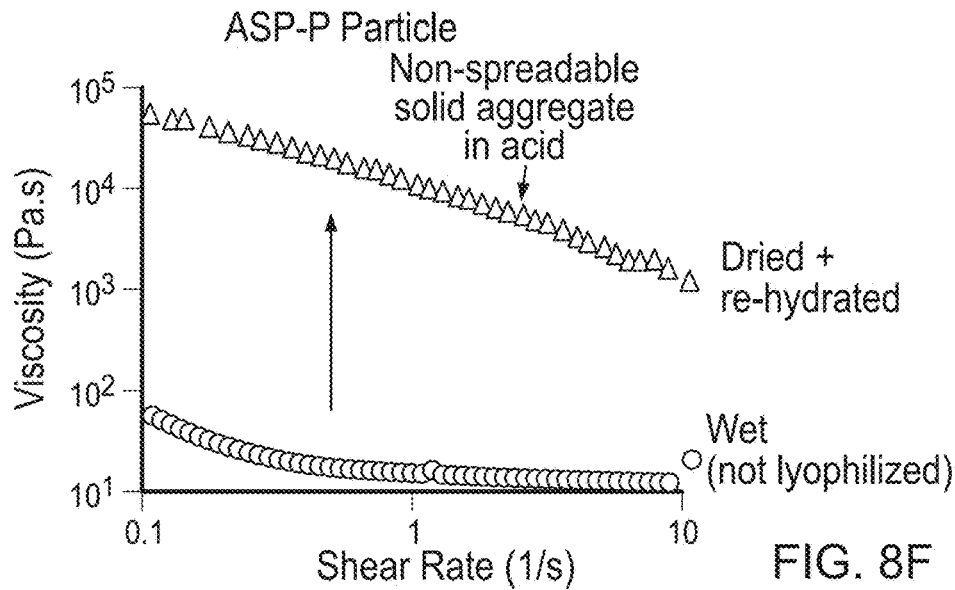
Figure 8G:
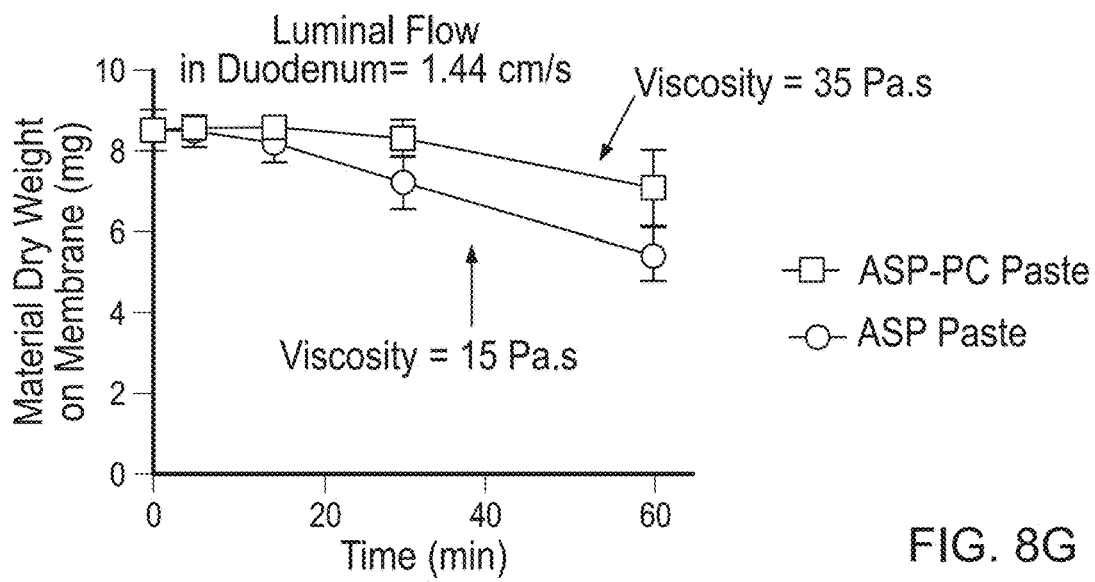
Figure 10A:
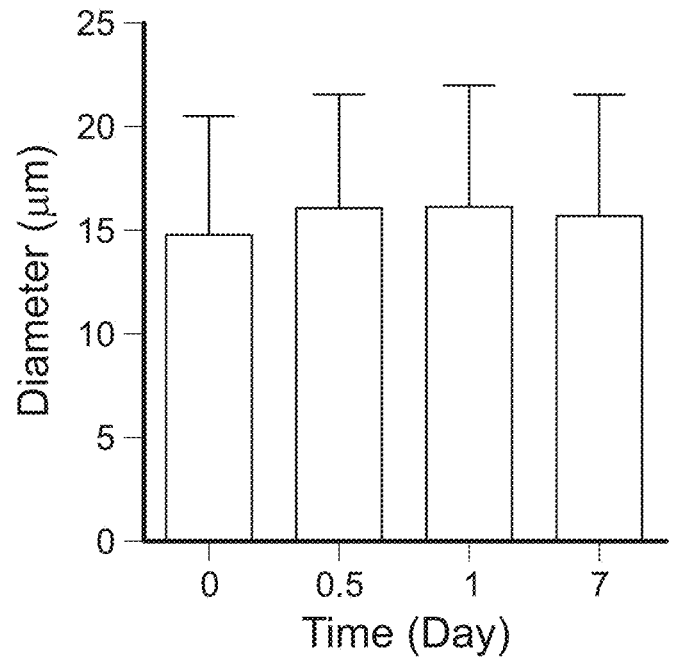
FIGS. 10A and 10B are a set of bar graphs showing the stability of ASP-PC particles in water for 7 days and after 5 cycles of drying/re-wetting, respectively.
Figure 10B:
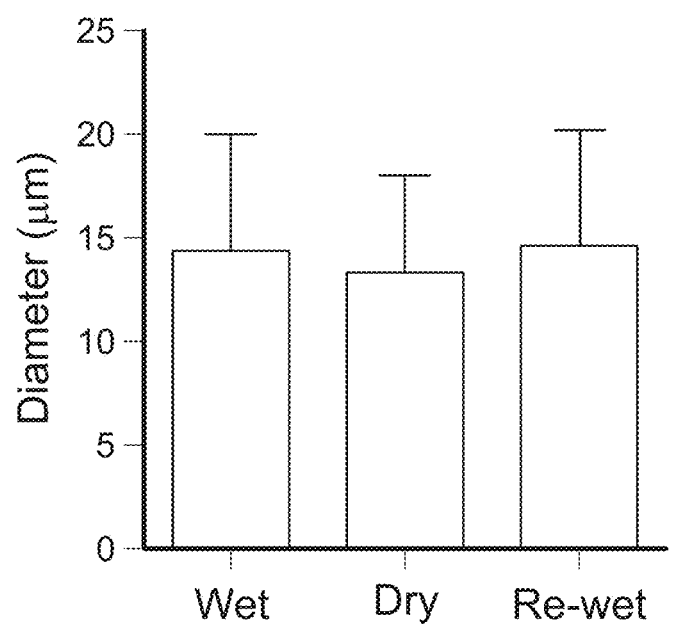

The incorporated carrageenan enables effective re-hydration of the dried particles to restore the ability to form an effective barrier coating. Specifically, the ASP-PC pastes exhibited a similar viscosity profile in the wet state before and after particle lyophilization (FIG. 8E) compared to dried carrageenan-free ASP-P particles that failed to restore its viscosity following re-hydration and formed a non-spreadable solid aggregate (FIG. 8F). Given that the highly sulfated polymer ι-carrageenan strongly interacts with sucralfate, re-hydrated ASP-PC showed higher viscosity compared to ASP paste (~2.3-fold higher for ASP-PC particles containing 0.1 w/w % carrageenan), and consequently exhibited higher resistance to shear stress in simulated duodenal flow (flow rate=1.44 cm/s (C. M. Malbert et al., J. Physiol., 409, 371-384) for 60 minutes, (FIG. 8G). In addition, the phosphate ion and carrageenan containing rehydrated sucralfate formulation showed excellent stability in water for over 7 days and during multiple drying/wetting cycles (tested for 5 cycles, see FIGS. 10A and 10B) indicating the potential for long shelf life.

Example 4

Inhibition of Glucose Absorption by Sucralfate Based Microparticulate Composition Methods To evaluate the in vivo effect of ASP-PC on postprandial glucose absorption, Sprague-Dawley (SD) rats were pre-gavaged with the particles and tested using the Oral Glucose Tolerance Test (OGTT) method. In standard OGTT experiments, SD rats were fasted overnight (starting time: 7 pm the prior day, duration: 15 hour) and gavaged with saline, ASP-PC or sucralfate (starting time: 10 am the next day, dose: 500 mg/kg rat, 3 times, 1-hour apart for each gavage) and 0.5 g/ml glucose solution (2 g/kg rat) was gavaged after 1 hour to measure the change in glucose level for 90 minutes (starting time: 1 pm, n=8 per arm). For shorter fasting time, the rats were fasted for 5 hour (starting time: 7 am the same day of OGTT) and gavaged with saline or ASP-PC (starting time: 12 am the same day, dose: 500 mg/kg rat, 3 times, 1-hour apart for each gavage). Blood was collected from the tail vein to measure blood glucose level using a glucometer (OneTouch UltraSmart, LifeScan Inc., USA). Statistical significance was determined using a paired Student t-test. Results were considered significant when $p \leq 0.05$.

Results

Figure 11A:
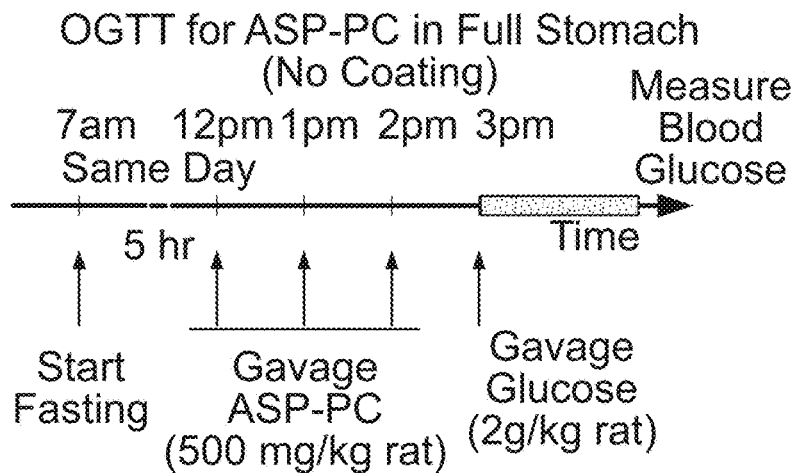
FIGS. 11A-11I display the oral glucose tolerance test protocol (OGTT) and results.
Figure 11B:
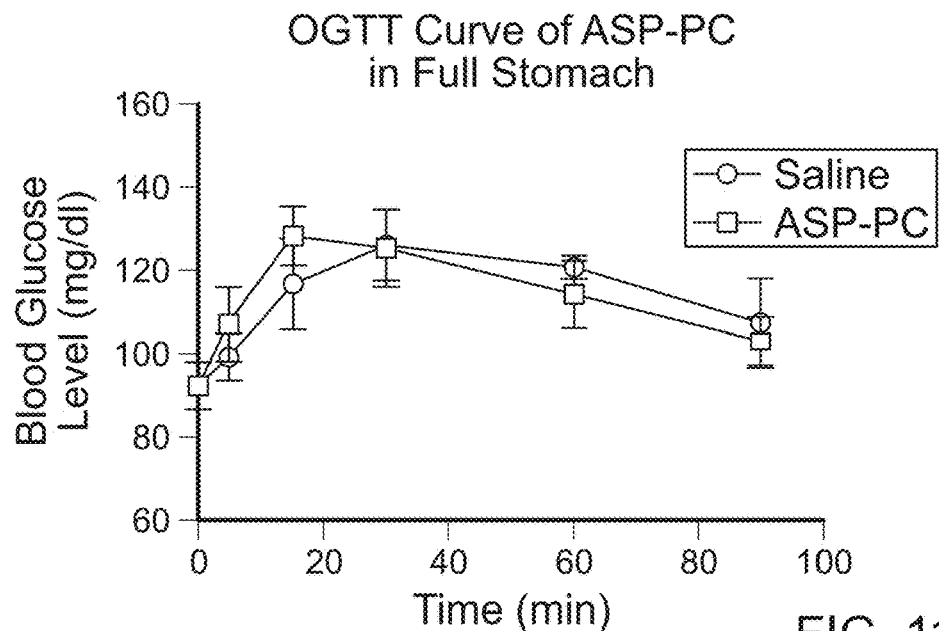
Figure 11C:
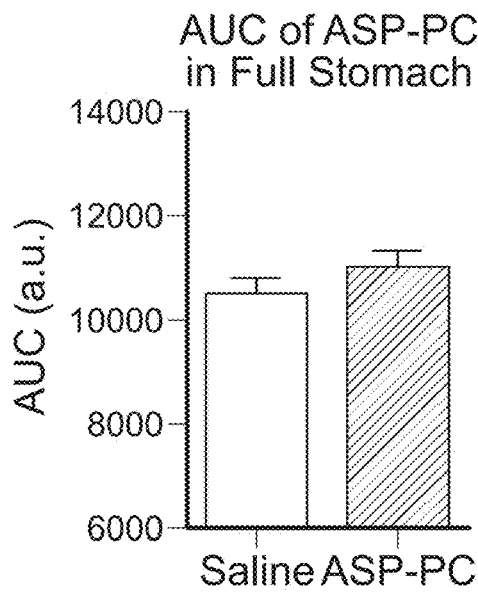
Figure 11D:
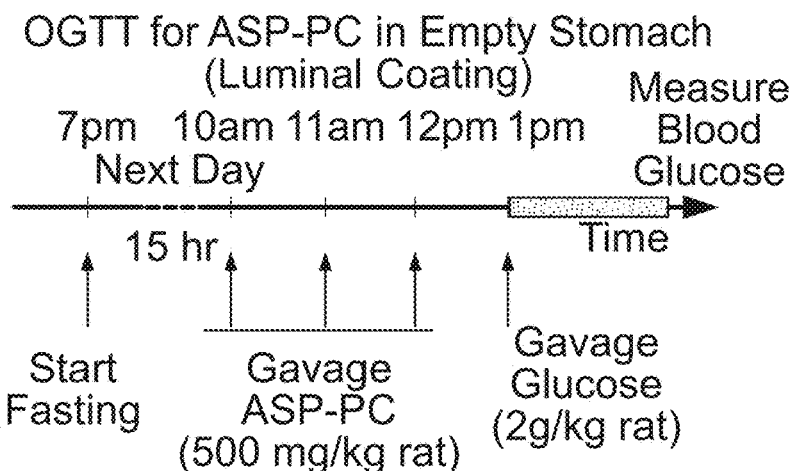
Figure 11E:
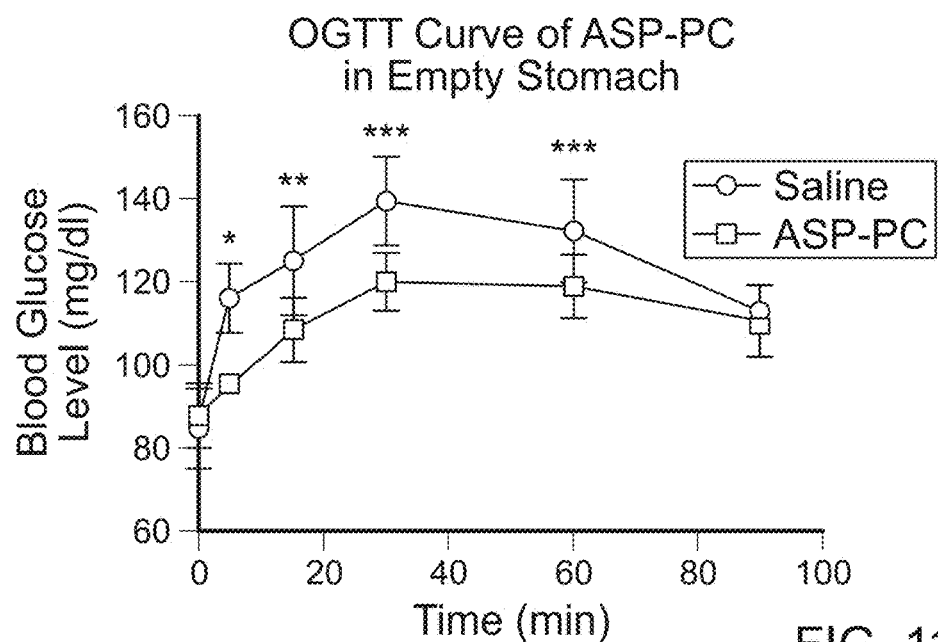
Figure 11F:
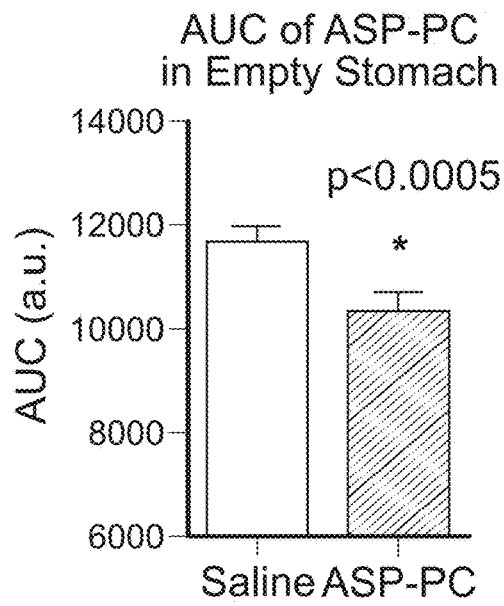

To demonstrate the luminal coating of ASP-PC particles on the intestine and the resultant effect on glucose homeostasis, two sets of in vivo experiments were performed: 1) administration of ASP-PC particles into rats whose stomachs were full of food, and 2) administration into rats whose stomachs contained less food or were empty. For gastric/duodenal ulcer treatment, clinical recommendations are to use sucralfate in an empty stomach for the maximum effect because residual food within the stomach blocks the luminal sucralfate coating. ASP-PC particles were gavaged in Sprague-Dawley (SD) rats fasted for 5 hour (FIGS. 11A, 11B, and 11C) or 15 hour (FIGS. 11D, 11E, and 11F) (dose: 500 mg/kg rat, 3 times, 1-hour apart for each gavage).

Figure 11G:
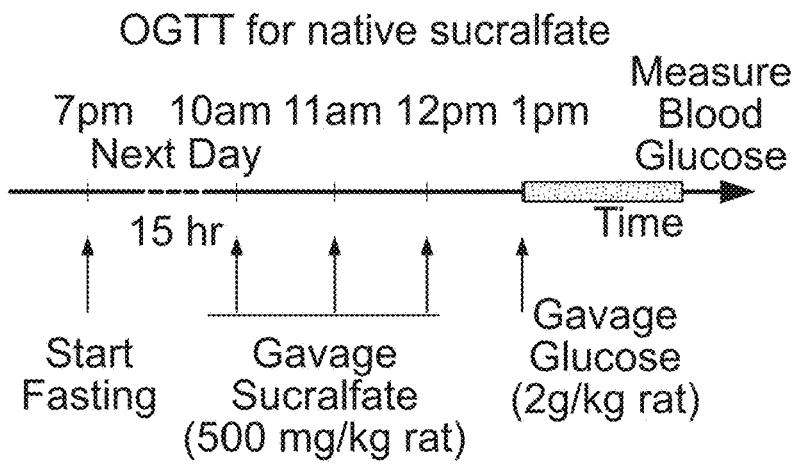
Figure 11H:
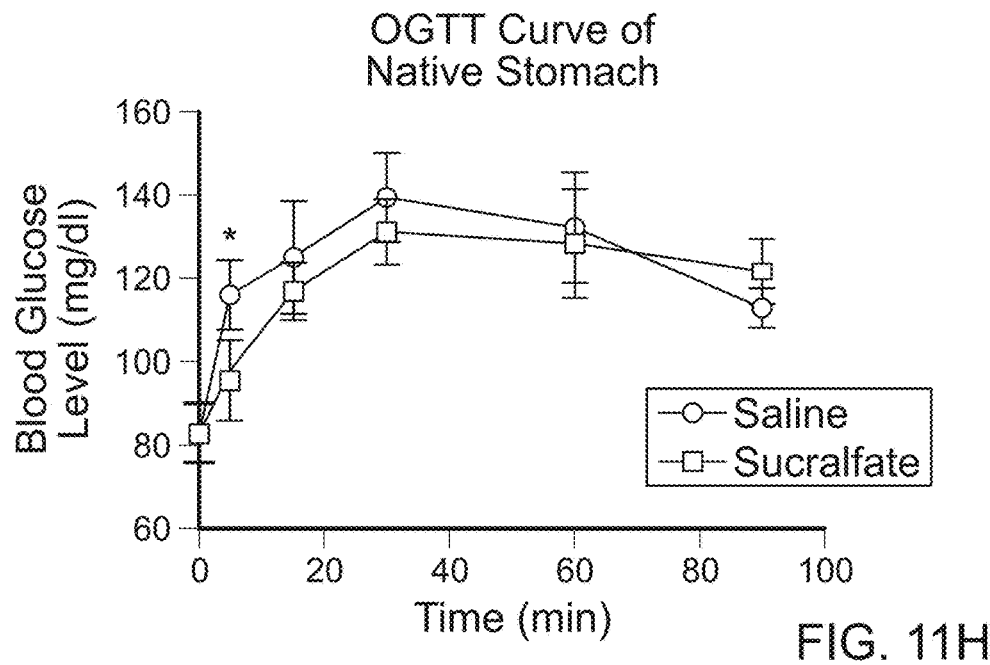
Figure 11I:
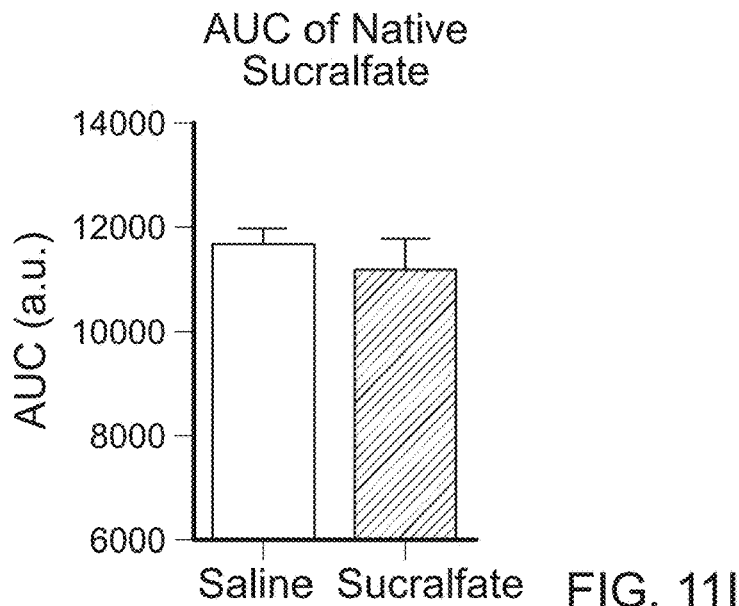

After 1 hour, the rats were subjected to a standard OGTT with 2 g/kg rat D-glucose gavage. The postprandial glucose responses of 5-hour fasted rats were similar to that of vehicle (saline)-gavaged rats in terms of both peak glucose values, and area under the curve (AUC). However, in rats with longer 15-hour fasts, pre-treatment with ASP-PC showed significantly lowered blood glucose levels at every time point throughout the experiment (in paired student t-test, $p<0.05$ in every time point up to 60 minutes). The area under curve (AUC) was also significantly decreased in the ASP-PC treatment arm (10.7% decrease compared to saline gavage controls, $p<0.003$) indicating that the luminal coating of ASP-PC quickly and effectively lowers the magnitude of postprandial glucose responses; an observation resembling that of RYGB. These data suggest that the compositions provided herein would promote weight loss in a subject. In addition, given that ASP-PC showed higher resistance to shear stress compared to sucralfate (FIG. 8G), the engineered ASP-PC particles exhibited a significantly reduced glucose absorption compared to native sucralfate. When native sucralfate was gavaged into the rats (dose: 500 mg/kg rat, 3 times, 1-hour apart for each gavage) (FIG. 11G), the 5-minutes glucose level was significantly lowered following OGTT (116.5±9.1 mg/dl for saline and 97.8±10577.3 mg/dl for sucralfate; $p<0.003$), however, the peak glucose values were similar at all other time points (FIG. 11H). The area under curve (AUC) was also similar between sucralfate and saline treated groups (FIG. 11I).

Example 5

Use of Acidified Sucralfate-Based Microparticulate Composition for the Treatment of Obesity To further evaluate the weight loss properties of sucralfate based microparticulate compositions experiments using two groups of rats are performed. In the first group, Sprague-Dawley (SD) rats receive a Western Diet (Research Diets DB12079B, 43% carbohydrate, 41% fat) which leads to obesity. This is the diet-induced obesity (DIO) model. In the second group, Zucker Diabetic Fat (ZDF) rats (the model of obesity-induced type 2 diabetes (T2DM) based on a leptin receptor mutation) are fed a Western diet. Both study groups (SD and ZDF) have three experimental arms, each representing a different mode of ASP-PC administration. In the first experimental arm, ASP-PC is added to the rodent water bottle. In the second arm, ASP-PC is added to the rodent chow, while in the third arm, ASP-PC is gavaged 2-3 times a day to the animal. Food and water intake is monitored daily for all animals. Each experimental arm is compared to a control group to observe changes in weight and intra-abdominal fat.

After treatment periods varying between 2-16 weeks, the rate of weight gain is calculated for each group. Glucose homeostasis is assessed using fasting blood glucose, oral glucose tolerance test (OGTT), and HbA1C assay. Liver fat content is assessed at harvest with the Folch technique, a method to calculate liver fat percentage as a ratio of dry fat mass and wet liver mass. Abdominal visceral fat content is assessed by the weight of peri-renal and epididymal fat pads at harvest as well as magnetic resonance imaging (MRI).

Example 6

Mucoadhesive Coating

Methods

Use of ASP-PC for altering nutrient exposure to the intestinal mucosa requires formation of an in vivo mucoadhesive layer on the intestinal wall. To confirm the formation of ASP-PC pastes with stomach acid and to demonstrate coating of ASP-PC on the intestine in vivo we administered ASP-PC into mice after residual food was eliminated.

In these experiments, SD rats were gavaged with ASP-PC particles and their GI tracts were harvested. Briefly, the rats were fasted overnight (starting time: 7 pm the prior day, fasted for 15 hours) and gavaged with 1 mL saline or lyophilized ASP-PC re-suspended in 1 mL normal saline (start time: 10 a.m. the next day, dose 500 mg/kg rat, 1 time, n=5 for each arm). After 1 hour, the stomach, duodenum, and three different parts of jejunum (each 20-cm apart) were harvested and carefully opened to expose the luminal surface, and then stained with an aqueous fluorescent quinine sulfate solution (1 mg/mL, pH 1.0) that is known to specifically bind to the acidified sucralfate pastes, and washed twice with DDW (pH 7.0). The stained stomach and bowels were placed onto glass slides and the fluorescence was visualized using an epifluorescent upright microscope (Nikon 80$i$). The stained tissues are imaged under UV light in a dark environment. The images were randomly acquired (n=8) for each sample. Statistical significance was determined using an unpaired Student t-test. The results were considered significant when $p \leq 0.05$.

Results

Figure 12A:
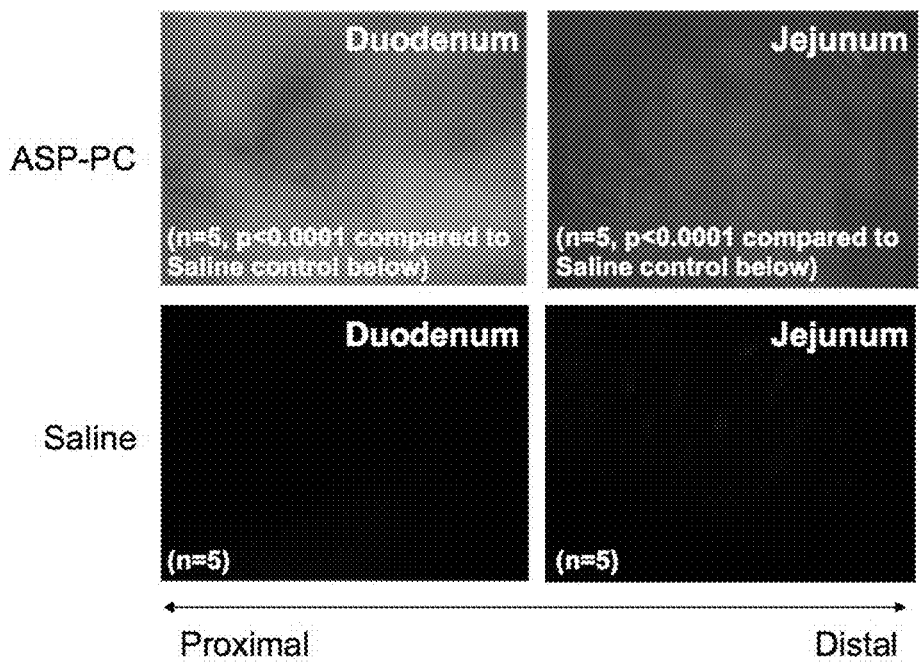
FIGS. 12A-12B display data showing the ability of ASP-PC to coat the duodenum and jejunum of rats after oral administration.
Figure 12B:
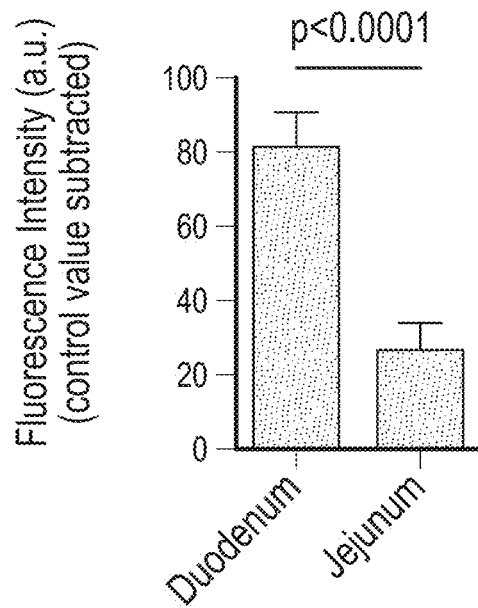

The fluorescent microscope images of the duodenum and jejunum from the ASP-PC-treated rats show that treatment with ASP-PC results in a continuous green layer in the duodenum and jejunum (FIG. 12A), while such a layer is not formed in the control rats administered saline, suggesting the gavaged acid-activated ASP-PC particles formed sticky paste and flowed distally to form a luminal coating. Also, there is more coating in the stomach and proximal gut (duodenum) than distal segment (jejunum) ($p<0.0001$, FIG. 12B) following ASP-PC administration that reflects the cranio-caudal distribution of ASP-PC paste. These data suggest that the composition provided herein will effectively coat the GI tract of a subject, thus resulting in a decrease in the absorption and/or uptake of nutrients (e.g., glucose, fats, and/or carbohydrates) by the GI tract of a subject. These data also confirm the desired higher concentrations in the proximal bowel to reduce nutrient absorption.

Example 7

Modulation of Cranio-Caudal Distribution and Retention Time Via Altering Viscosity and Charge The level of mucoadhesion on the gastrointestinal mucosa affects the residence time and cranio-caudal distribution of the acidified sucralfate paste. The mucoadhesive properties of the new compositions are fine-tuned to alter properties of the coating to maximize nutrient blockage by altering the cohesive strength and interaction of the components, e.g., by varying the viscosities and charge. Compositions selected from the in vitro screening process are assessed in animal models for altered residence time/cranio-caudal distribution and glucose absorption. Below are potential strategies to achieve these goals.

In acidic solutions, the acidified sucralfate is partially hydrolyzed releasing aluminum ions within hydroxylated species to form a sticky paste. Given that the aluminum acts as a cross-linker to aggregate the sucrose sulfates into insoluble sticky pastes, the acidity of the reaction solution is a key determinant of the viscosity of sucralfate paste. To fabricate the aluminum-liberated paste, 300 mg of sucralfate are reacted in 3 ml of HCl solution. Three different HCl concentrations (0.1, 0.2, 0.3 N) are tested for releasing different amount of aluminum. The resultant dispersions are stirred vigorously until the powders are agglomerated together into a paste or completely dissolved (usually within 1-2 minutes).

The resulting pastes are further incubated under ambient conditions for 2 hours, and purified through washing with fresh 0.1 N HCl solutions (3×) and followed by washing with distilled water (3×). Ten mls of phosphate buffer (pH 7.4) are added to the vial containing the paste to buffer the pH and are vortexed (600 rpm) to provide a shear force for 5 minutes to generate the particles. The fabricated particles are extensively washed with water at least 5 times to remove excess particle coating material.

To compare the viscosity, the particles with different cross-linking densities are reformulated into a paste in simulated stomach acid (pH 1.0). The viscosities of the reformulated pastes are measured using a rheometer and are correlated with the aluminum cross-linker contents in the pastes measured using inductively coupled plasma atomic emission spectroscopy (ICP-AES). To compare the residence time of the different paste formulations, an in vitro flow-chamber assay with shear flow is used. Briefly, 1 ml of 1% particles with different cross-linker contents in simulated stomach acid is applied to mucin-coated cellulose nitrate membranes. The membranes are mounted in a flow chamber (height: 0.01 inch, width: 10 mm). To simulate the luminal flow in the duodenum, simulated stomach acid is infused at a rate of 1.44 cm/s (2.198 ml/min). Following 0, 5, 15, 30, and 60 min, each membrane is collected and lyophilized to measure the dry weight. This experiment is performed on 3 separate occasions (n=3). Given that the surface charge of the particles will significantly contribute to the initial interaction with mucosa, and the bulk charge will dominate the interaction after aggregation into paste form, we aim to explore the contribution from both surface and bulk charge of the ASP-PC particles.

To alter surface charge of ASP-PC particles, the phosphate ions on the particle surface are substituted with other particle stabilizers with different charges. Given that substitution of the entire surface can also affect particle properties other than surface charge (e.g., particle stability and barrier function), we aim to modify a portion of the particle surface. The stabilizers are selected from FDA-approved GRAS (generally recognized as safe) materials including positive-charged polymers (e.g., chitosan), neutral polymers (e.g., cellulose derivatives, gellan gum, and PEG) and negative-charged polymers (e.g., pectins, carrageenans, and carboxymethylcellulose). Briefly, to fabricate surface modified ASP-PC particles, 500 mg of sucralfate is reacted in 5 ml of 0.1N HCl, incubated for 2 hours under ambient conditions and washed in DDW three times. Ten milliliters of particle stabilizer solution in phosphate buffer (pH 7.4) is added in the vial containing the paste and vortexed (600 rpm) to provide shear force for 5 min. The fabricated particles are extensively washed with water at least 5 times to remove excess particle coating material. The surface charge of the particles is measured using zeta potential analyzer. The mucoadhesion of the particles with different stabilizers are measured by comparing the relative adhesion on simulated mucosa. Briefly, 10 mg of each particle formulation is suspended in 1 ml of DDW (pH 7.0) and is added on a cellulose nitrate membrane that is coated with mucus in simulated stomach acid (pH 1.0). After 5 min, the membrane is dried to measure the particle adhesion.

To alter bulk charge (inside the particles) and the resultant paste in stomach acid, we aim to incorporate polymers with different charges selected from FDA's GRAS list. Given that polymers with inherent gelling properties or potential strong interaction with sucralfate can also alter the viscosity of reformulated paste in acid, the polymers with different charges are selected from the list of non-gelling polymers including positive-charged polymers (e.g., chitosan), and neutral-charged polymers (e.g., cellulose derivatives, PEG). Negative-charged polymers including sulfated polymers (e.g., carrageenan, heparin) are excluded given that they can strongly interact with sucralfate in acid and significantly alter the viscosity. Briefly, to incorporate polymers into the ASP-PC particles, 300 mg of sucralfate is reacted in 3 ml of a candidate polymer solution in HCl solution (pH 1.0). The resultant dispersion is stirred vigorously until the powder was agglomerated together into a paste or completely dissolved (usually within 1-2 min). The paste is further incubated under ambient conditions for 2 hours. The supernatant is removed and the paste is purified through washing with fresh 0.1 N HCl solutions (3×) and followed by distilled water (3×). Ten milliliter of phosphate buffer (pH 7.4) are added in the vial containing the paste and vortexed (600 rpm) to provide shear force for 5 min. The fabricated particles are extensively washed with water at least 5 times to remove excess particle coating material. To compare the residence time of the particles with different bulk charges, in vitro flow-chamber assay with shear flow is used as described above.

The compositions selected from the in vitro screening processes are anticipated to show altered cranio-caudal distribution and altered postprandial glucose response. Thus, it is of primary importance to assess the behavior of the engineered sucralfate formulations when they are orally administered to a subject. We will first use more accessible normal Sprague-Dawley (SD) rats to visualize cranio-caudal distribution and further use Zucker Diabetic Fat (ZDF) rats to correlate with the altered glucose responses in diabetic model.

The cranio-caudal distribution of the engineered sucralfate particles are visualized by staining the paste on GI tract with fluorescent quinine hemisulfate (ex=310 nm, em=450 nm). Quinine hemi sulfate is used to selectively stain the sucralfate-based pastes given its strong interaction with sucralfate and strong fluorescence in low pH. Normal SD rats are orally administered with the selected compositions in pre-determined dosage schedules and proximal gastrointestinal tract are harvested for imaging under UV light. In detail, SD rats are fasted overnight (starting time: 7 pm the prior day) and gavaged with saline, or a selected barrier coating composition (starting time: 10 am the next day, dose: 100-500 mg/kg rat, 1-3 times, 1-hr apart for each gavage). Stomach and proximal bowel including are harvested after 1 hour, small bowel is dissected into 10 cm segments and opened carefully to expose the luminal surface, and dipped into aqueous quinine sulfate solution (1 mg/ml, pH 1.0) with dip-wash in distilled water.

The stained tissues are imaged under UV light in a dark environment and analyzed for the area of coverage for each segment in GI tract. To assess kinetic change of the cranio-caudal distribution, the SD rats are gavaged with the selected composition according to the dosage schedule described above, and tissues from GI tract are harvested after longer time period (2-5 hr) for further imaging analysis.

To evaluate the in vivo effect of the selected materials on postprandial glucose absorption, SD rats are pre-gavaged with each material and tested using the oral glucose tolerance test (OGTT) method. In standard OGTT experiments, SD rats are fasted overnight (starting time: 7 pm the prior day, duration: 15 hours) and gavaged with saline, or a selected barrier coating formulation (starting time: 10 am the next day, dose: 100-500 mg/kg rat, 1-3 times, 1-hr apart for each gavage) and 0.5 g/ml glucose solution (2 g/kg rat) are gavaged after 1 hour to measure the change in glucose level for 90 min (starting time: 1 pm, n=8 per arm). Blood is collected from the tail vein to measure blood glucose level using a glucometer as a measure of the impact of different dosages (e.g., dose amount, timing) to analyze the contribution of the blocking of each segment.

Example 8

Modulation of Cranio-Caudal Distribution and Retention Time Via Encapsulating Acid-Treated Microparticles in Enteric or Non-Enteric Coated Formulation Method Given that each segment of gastrointestinal tract (e.g., stomach, duodenum and jejunum) has its own unique discrete functions including nutrient sensing and hormone transduction, cranio-caudal distribution of the physical barrier affects the physiological impact. Selective coating of the physical barrier on each segment can modulate the physiological impact on glucose homeostasis. To evaluate this in a rat model, enteric coated capsules (for duodenum and jejunum) and non-enteric coated capsules (for stomach) are filled with the sucralfate-based microparticles that are pre-treated with acid. Briefly, 500 mg of sucralfate-based microparticles are added with 5 ml of simulated stomach acid (pH 1.0), and the resultant paste is filled into gelatin capsule for rats (maximum dose: 500 mg/kg rat). For enteric coating, Eudragit® is dispersed in water in the presence of plasticizer (e.g., triethyl citrate) and anti-tacking agent (e.g., talc), and gently stirred with a conventional stirrer. The suspension is filtered through a 0.5 mm sieve and is coated on the prepared gelatin capsule using spray coater.

For each segment in gastrointestinal tract, Eudragit® E100, Eudragit® E12, 5 or Eudragit® E PO is used for targeting stomach (non-enteric coating). Eudragit® L30 D-55 or Eudragit® L100-55 is used for targeting the duodenum, and Eudragit® L100 or Eudragit® L12, 5 is used for targeting the jejunum. If necessary, Eudragit® S100, Eudragit® S12, 5 or Eudragit® FS30D is used to target the ileum. Normal SD rats are gavaged with a capsule targeting each segment and gastrointestinal tissue will be harvested for imaging to confirm the barrier coating formation. Briefly, SD rats are fasted overnight (starting time: 7 pm the prior day) and gavaged with a selected enteric or non-enteric coated capsule (starting time: 10 am the next day, dose: 100-500 mg/kg rat, 1-3 times, 1-hr apart for each gavage).

Tissues from GI tract are harvested after 1 hours, dissected into segments (stomach, duodenum, proximal bowel), opened carefully to expose the luminal surface, and dipped into aqueous quinine sulfate solution (1 mg/ml, pH 1.0) with dip-wash in distilled water. The stained tissues are imaged under UV light in a dark environment and analyzed for the area of coverage for each segment in GI tract. To assess kinetic change of the cranio-caudal distribution, the SD rats are gavaged with the selected composition according to the dosage schedule described above, and tissues from the GI tract are harvested after longer time period (2-5 hours) for further imaging analysis.

Concomitantly with imaging the nutrient barrier coating on the GI tract using enteric or non-enteric coated capsules, the metabolic impact of the orally administered the selected barrier coating on each segment can be determined to help estimate the effective capsule formulation for further testing in this diabetic animal model. To evaluate the in vivo effect of the selected capsule on postprandial glucose absorption, SD rats are pre-gavaged with each capsule and tested using the oral glucose tolerance test (OGTT) method. In standard OGTT experiments, SD rats are fasted overnight (starting time: 7 pm the prior day, duration: 15 hours) and gavaged with saline, or a selected barrier coating formulation (starting time: 10 am the next day, dose: 100-500 mg/kg rat, 1-3 times, 1-hr apart for each gavage) and 0.5 g/ml glucose solution (2 g/kg rat) is gavaged after 1 hour to measure the change in glucose level for 90 min (starting time: 1 pm, n=8 per arm). Blood is collected from the tail vein to measure blood glucose level using a glucometer to examine the impact of selective barrier coating on each segment in GI tract and match this with the cranio-caudal distribution imaging results to analyze the contribution of the blocking of each segment.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method of treating a subject, the method comprising:
    administering to the subject a composition comprising an acidified aluminum cross-linked sulfated agent and a particle stabilizer cross-linked with a humectant, wherein the particle stabilizer is the same as or different than the humectant, wherein the subject has type II diabetes, obesity, insulin resistance, hyperlipidemia, or hypertension, and wherein, in the presence of acid, the composition forms a mucoadhesive coating on mucosa of at least a portion of the subject's gastrointestinal tract to thereby modulate nutrient absorption by the subject.

2. The method of claim 1, wherein the acidified aluminum cross-linked sulfated agent comprises sucralfate, carrageenan, sulfated dextran, sulfated dextrin, sulfated amylopectin, sulfated amylose, sulfated cellulose, chondroitin sulfate, glucose sulfate, sucrose sulfate, or raffinose sulfate.

3. The method of claim 1, wherein the composition further comprises an acid.

4. The method of claim 3, wherein the acid comprises sodium citrate, ascorbic acid, boric acid, hydrochloric acid, or ascetic acid.

5. The method of claim 3, wherein the composition is formulated for controlled release, and the composition forms the coating on at least portion of the subject's duodenum.

6. The method of claim 5, wherein the subject consumes food after administration of the composition, and the coating modulates nutritional absorption in the subject.

7. The method of claim 1, wherein the method reduces glucose absorption by the subject.

8. The method of claim 1, wherein the subject has type II diabetes or obesity.

9. The method of claim 1, wherein the composition further comprises a drug or antimicrobial material.

10. The method of claim 1, wherein the composition is in the form of a capsule or a tablet.

11. The method of claim 1, wherein an aluminum/sulfate ratio in the composition is greater than or equal to 1.27 and less than or equal to 1.83.

12. The method of claim 1, wherein the administration is oral.

13. A method of treating a subject, the method comprising:
administering to the subject a composition comprising an acidified aluminum cross-linked sulfated agent, a particle stabilizer cross-linked with a humectant, and an acid, wherein the particle stabilizer is different than the humectant, and wherein the composition forms a mucoadhesive coating on mucosa of at least a portion of the subject's gastrointestinal tract.

14. The method of claim 13, wherein the composition is formulated for controlled release, and the composition forms the coating in at least a portion of the subject's duodenum.

15. The method of claim 13, wherein the method reduces glucose absorption by the subject.

16. The method of claim 13, wherein the subject has type II diabetes, obesity, insulin resistance, hyperlipidemia, or hypertension.

17. The method of claim 13, wherein the acidified aluminum cross-linked sulfated agent comprises sucralfate, carrageenan, sulfated dextran, sulfated dextrin, sulfated amylopectin, sulfated amylose, sulfated cellulose, chondroitin sulfate, glucose sulfate, sucrose sulfate, or raffinose sulfate.

18. The method of claim 13, wherein the acid is a powdered acid.

19. The method of claim 13, wherein the composition further comprises a drug or antimicrobial material.

20. The method of claim 13, wherein the administration is oral.

21. A method of treating a subject, the method comprising:
administering to the subject a therapeutic agent and a composition comprising an acidified aluminum cross-linked sulfated agent and an acid, wherein the composition is in the form of a capsule or a tablet, wherein the composition forms a mucoadhesive coating on mucosa of at least a portion of the subject's gastrointestinal tract, and wherein the therapeutic agent is a diabetes therapeutic agent or an obesity therapeutic agent.

22. The method of claim 21, wherein the composition further comprises a particle stabilizer, a humectant, or both a particle stabilizer and a humectant.

23. The method of claim 21, wherein the acid is a powdered acid.

24. The method of claim 21, wherein the composition is administered with a diabetes therapeutic agent chosen from insulin, metformin, sulfonylurea, an alpha-glucosidase inhibitor, a thiazolidinedione, an amylin analog, a bile acid sequestrant, a DPP-4 inhibitor, a dopamine agonist, an incretin mimetic, a non-sulfonylurea secretagogue, or a meglinitide.

25. The method of claim 21, wherein the administration is oral.

* * * * *

UNITED STATES PATENT AND TRADEMARK OFFICE
CERTIFICATE OF CORRECTION

| | |
|---|---|
| PATENT NO. | : 11,524,024 B2 |
| APPLICATION NO. | : 16/890913 |
| DATED | : December 13, 2022 |
| INVENTOR(S) | : Jeffrey M. Karp et al. |

It is certified that error appears in the above-identified patent and that said Letters Patent is hereby corrected as shown below:

In the Specification

Column 1, Line 15, insert -- STATEMENT OF FEDERALLY SPONSORED RESEARCH
This invention was made with government support under Grant Nos. DK084064, and RR025757 awarded by the National Institutes of Health. The government has certain rights in the invention. --

Signed and Sealed this
Sixteenth Day of May, 2023

Katherine Kelly Vidal
*Director of the United States Patent and Trademark Office*